(12) United States Patent
Zhou et al.

(10) Patent No.: US 8,143,396 B2
(45) Date of Patent: Mar. 27, 2012

(54) 1-[2',3'-DIDEOXY-3'C-(HYDROXYMETHYL)—BETA-D-ERYTHRO-PENTOFURANOSYL] CYTOSINE DERIVATIVES AS HIV INHIBITORS

(75) Inventors: Xiao-Xiong Zhou, Huddinge (SE); Christer Sahlberg, Huddinge (SE)

(73) Assignee: Medivir AB, Huddinge (SE)

( * ) Notice: Subject to any disclaimer, the term of this patent is extended or adjusted under 35 U.S.C. 154(b) by 0 days.

(21) Appl. No.: 12/982,667

(22) Filed: Dec. 30, 2010

(65) Prior Publication Data

US 2011/0112294 A1 May 12, 2011

Related U.S. Application Data

(62) Division of application No. 11/994,633, filed as application No. PCT/EP2006/063919 on Jul. 5, 2006, now Pat. No. 7,888,367.

(30) Foreign Application Priority Data

Jul. 7, 2005 (GB) .................................. 0513835.9

(51) Int. Cl.
*C07D 239/22* (2006.01)
(52) U.S. Cl. ...................................... 544/317
(58) Field of Classification Search .................... 544/317
See application file for complete search history.

(56) References Cited

FOREIGN PATENT DOCUMENTS

| WO | WO-2006/07004 | A2 | 1/2006 |
| WO | WO 2006/070004 | * | 7/2006 |

OTHER PUBLICATIONS

Mauldin, et al., Bioorganic & Medicinal Chemistry, Elsevier Science Ltd, GB, vol. 6, No. 5, 1998, p. 577-585.
3GPP TS 33.102 V7.0.0 (Dec. 2005) 3G Security; Security architecture (Release 7).
3GPP TS 25.331 V7.1.0 (Jun. 2006) Radio Resource Control (RRC); Protocol Specification (Release 7).

* cited by examiner

*Primary Examiner* — Deepak Rao
(74) *Attorney, Agent, or Firm* — Birch, Stewart, Kolasch and Birch, LLP

(57) ABSTRACT

Novel bicyclic tetrahydrofuran compounds and derivatives, and pharmaceutically acceptable salts thereof, according to the formula:

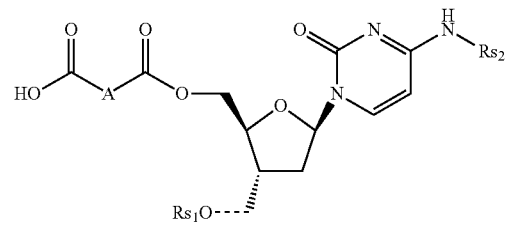

These compounds have utility in the treatment of retroviruses such as HIV, especially reverse transcriptase mutant which allow an obligate chain terminating nucleoside- or nucleotide-phosphate to be excised from the nascent DNA strand by ATP or pyrophosphate-mediated excision.

6 Claims, 5 Drawing Sheets

1-[2', 3'-DIDEOXY-3' C-(HYDROXYMETHYL)—BETA-D-ERYTHRO-PENTOFURANOSYL] CYTOSINE DERIVATIVES AS HIV INHIBITORS

This application is a Divisional of application Ser. No. 11/994,633 (now U.S. Pat. No. 7,888,367) filed on Feb. 22, 2008, and for which priority is claimed under 35 U.S.C. §120; and this application claims priority of Application No. PCT/EP2006/063919 filed on Jul. 5, 2006 and to Application No. 0513835.9 filed in Great Britain on Jul. 7, 2005 under 35 U.S.C. §119; the entire contents of each are hereby incorporated by reference.

TECHNICAL FIELD

This invention relates to novel bicyclic tetrahydrofuran derivatives and their use in the treatment of retroviruses such as HIV, especially drug escape mutations.

BACKGROUND ART

Unlike other HIV antivirals, such as protease inhibitors or non-nucleoside reverse transcriptase inhibitors, nucleoside reverse transcriptase inhibitors (NRTI) are pharmacologically inactive in their administered form and require phosphorylation by host cellular kinases to produce the active triphosphate metabolite. This triphosphate form resembles the naturally occurring deoxynucleotide triphosphate substrates of the viral reverse transcriptase and competes for HIV-1 RT binding and incorporation into viral DNA.

All NRTI s approved for the treatment of HIV, and the vast majority of all other NRTIs proposed in the patent or academic literature, lack a 3'-hydroxy function on the ribose moiety of the nucleoside. Examples include zidovudine (AZT), stavudine (d4T), lamivudine (3TC), zalcitabine (ddC), abacavir (ABC), didanosine (ddI) and tenofovir (TNF) (the latter being typically administered as the disoproxil fumarate prodrug). Upon phosphorylation, such a nucleoside or nucleotide analogue is covalently bonded by the reverse transcriptase enzyme to the nascent DNA strand, but the lack of a 3'-hydroxyl function in the nucleoside or nucleotide prevents further attachment of additional nucleotides. These NRTIs therefore terminate viral DNA strand prolongation, thereby leading to inhibition of HIV replication (Mitsuya et al 1990, Jacob Molina et al 1993, Reardon 1993).

The cornerstone of all current antiretroviral therapies (ART) is the use of NRTIs. NRTIs, however, are only able to retard HIV propagation in the blood stream and to date have been unable to eradicate HIV from patients. HIV operates by inserting its DNA into latent host cells involved in human immunologic memory. This mode of infection implies that patients are forced to take HIV antivirals lifelong in order to prevent the HIV titre from bouncing back after therapy has ended.

In practice, however, the effective administration period of a particular HIV drug for a given patient is dramatically limited by the emergence of "escape mutants." An escape mutant is a virus that contains a discrete cluster of mutations that produces drug resistance and allows it to proliferate in the presence of the drug. Escape mutants arise in a patient due to the selective pressure of the particular antiviral(s) that the patient is taking. As a consequence, a drug's effective administration period is dependent on how quickly escape mutants arise and proliferate.

In countries consistently prescribing HIV antivirals it is becoming increasingly evident that the primary infection in new cases of HIV is often not with wild type HIV, but rather with a strain of HIV which is already partly or multiply resistant to the current antivirals. In other words, escape mutants which are generated in situ in infected patients can also be spread to naive patients by lateral or vertical transmission. This in turn means that even some patients who would otherwise be classified as treatment-naive are already infected with virus resistant to conventional first line therapies.

Multiple factors contribute to the selection of drug escape mutants including total HIV pool size, RT processivity and infidelity in viral genomic replication, viral fitness and multiple availabilities of target cells. By the late 1990s, evidence from long term use of combinations based on zidovudine (AZT) or stavudine (d4T) suggested that clusters of particular mutations in the RT were consistently generated. These mutation clusters are the prototype now known as Thymidine Analogue Mutations (TAMs). The presence of TAMs enhanced the likelihood of selecting further mutations and led to the development of more advanced NRTI resistance phenotypes that were not clearly within the family of thymidine analogues. Such phenotypes are now known as Nucleoside Analogue Mutation (NAM) and Multiple Drug Resistance (MDR) HIV.

Hypothesis for NRTI Resistance

AZT was the first antiretroviral to be widely used and not surprisingly was the first to generate escape mutants (Larder et al., 1989). However in view of the large number of mutations throughout the HIV genome in typical patient isolates it is not possible to produce the resistance phenotype in vitro using a recombinant RT enzyme bearing the particular TAM. As a consequence, the mechanisms through which TAMs confer resistance have not been straightforward to elucidate. Various hypothetical models and theoretical predictions for the mechanism behind TAM resistance have been predicated on the involvement of nucleophilic attack by a pyrophosphate donor (Boyer et al, 2002 and Meyer et al, 2002). Presumably RT translocation theory is a key step in understanding the TAM associated resistance mechanism. This was, however, poorly understood until the end of 2002 because the RT pre- and post-translocation intermediates are transient and short-lived and not readily accessed experimentally.

The modern understanding of RT translocation theory holds that RT catalyzed DNA polymerization takes place in a detailed cascade fashion as illustrated in FIG. 3, which is adopted from Sarafianos et al (2003). These steps are 1) Binding of the DNA substrate by free enzyme E positions the 3'-primer end at the P-site (Primer site).
2) Binding of a dNTP close to the N-site (dNTP site) forms an "open" ternary complex.
3) A "closed" ternary complex is formed by enzyme conformational changes.
4) Phosphodiester bond formation between the 3'-OH primer terminus and the alpha phosphate of the dNTP is accompanied by release of pyrophosphate (PPi) to form the pre-translocated RT complex at the N-site.
5) Translocation of the primer terminus from the N-site to the P-site by forming a post-translocated complex which is a prerequisite for the next dNTP binding and continuation of DNA synthesis.

If a DNA chain terminator nucleoside (NRTI) triphosphate (typically a nucleoside analogue which lacks a 3'-hydroxy function on the deoxyribose moiety) is used, it mimics its natural dNTP counterpart and binds to RT. After the analogous chemical processing, the incorporated NRTI forms a pre-translocation complex at the N-site of polymerization.

This terminates further DNA synthesis due to the lack of a 3'-hydroxyl primer on the NRTI's deoxyribose moiety.

In contrast, TAM-related RT mutations employ a different nucleotide incorporation mechanism compared to wild type RT. Specifically, the new mechanism results in the release (excision) of the NRTI incorporated at the primer terminus, abrogating the chain terminating activity of the NRTI. This new mechanism is dependent on the interplay between the accumulation of complexes in pre-translocated states (at the N-site) and the availability of ATP or pyrophosphate donors, which are often abundant at the site of infection, i.e. normal lymphocytes.

ATP or pyrophosphate does not normally participate in viral DNA-polymerization reactions, but the structure of a RT expressing a TAM-related resistant phenotype facilitates their entry into a site adjacent to a newly incorporated NRTI. The equilibrium between pre- and post-translocational kinetic species provides a mechanism to ensure free access of the primer terminus to the N-site and also allows simultaneous binding of the pyrophosphate donor ATP at the P-site after the incorporation of the NRTI chain terminator and the release of pyrophosphate. When this occurs, ATP (or pyrophosphate) attacks the phosphodiester bond which links the incorporated NRTI at the end of the DNA, resulting in removal of the NRTI via pyrophosphorolysis. When the pyrophosphate donor is ATP, the NRTI is released as a dinucleoside tetraphosphate product. FIG. 4 illustrates this "primer rescue" in an AZT-terminated DNA (adopted from ClinicCareOptions™).

It is now believed that two distinctive mechanisms are involved in the phenotypic resistance to NRTI (Sluis-Cremer et al, 2000). The first, known as "primer rescue" activity, is described immediately above. Here, the chain-terminating nucleotide is removed from the 3' end of the primer terminus through ATP-dependent or pyrophosphate-dependent pyrophosphorolysis. There is, however, another cluster of resistance phenotypes denoted as "discriminative mutants." These mutants have an RT with enhanced ability to discriminate between NRTIs and native dNTPs. In this case, the mechanism leads to RT which is able to preferentially choose the right substrate (i.e. native dNTP), thereby avoiding chain termination by an NRTI and ensuring the propagation of the viral genome.

Generation of Mutations in HIV

Retroviruses such as HIV have the potential for rapid genetic diversification. While this is an energetically inefficient process, it offers clear adaptive advantages to the organism. The replication machinery used by HIV is particularly error prone, generates a large number of mutations and has the potential to lead to accumulation of mutations when the organism is under selective pressure.

Generally, the vast majority of mutations generated by viral replication result in less viable enzymes. Here, the accumulation of a second and especially a third mutation is less probable because the population pool for the less viable mutant, within which the second mutation must accumulate, will be diluted by the faster multiplying wild type organism.

Yet more viable viral mutants can arise and expand by two possible pathways. The first occurs when there is rapid outgrowth of a highly resistant variant that is already present in the overall viral population. Most frequently this is a single point mutation that confers phenotypic resistance to a selective pressure. In the context of drug escape mutations examples include K103 rapidly induced by the non-nucleoside reverse transcriptase inhibitor nevirapine.

The second pathway occurs when there is continued viral replication in the presence of selective pressure. This allows the progressive accumulation of mutations that can then be expanded. In this case, the probability of mutation accumulation is related to the amount of virus replication that is occurring. That is, at higher viral loads (e.g. >200,000 copies/ml), accumulations of double mutations can occur. Accumulation of triple mutations, however, are rare and can only result as a consequence of a complex therapeutic regimen, typically involving several different drugs, that is challenging for the patient to adhere to. It is therefore extremely difficult for even a diligent patient to ensure that all active ingredients are present in the blood at levels above the necessary inhibitory concentrations over the full 24 hour period of each day "24 hour trough level". Here, temporary removal of any one of the selective pressures of drug treatment due to lapses in the administration/24 hour trough level of one or more drugs allows unbridled viral replication, thereby permitting the generation and establishment of many new mutants. When the selective pressure is once again applied (i.e. resumption of complex drug therapy), the few new mutants that have accumulated another point mutation which confers better drug resistance can expand in a manner similar to that seen for the first pathway (see above).

The discussion above focuses on accumulation of point mutations as opposed to, for example, deletion or addition mutations. Here, however, a scenario similar to that described for a triple mutation is applicable. That is, most deletion/addition mutations initially involve a single nucleotide. This has the effect of completely altering the downstream amino acid sequence of the encoded protein if the change occurs within the coding region and leads to a truncated and/or inactive protein. In order to preserve the reading frame and to alter the final protein by the deletion or addition of one single amino acid, three nucleotides must be deleted/added. Since inactive enzymes reduce the viability of an HIV organism, particularly if the enzyme affected is RT, the deletion/additions will not accumulate per se, but must occur simultaneously. In other words the equivalent of a triple mutation must occur in a single event, which is highly uncommon (see Boyer et al (2004) J Virol 78(18):9987-9997, which is hereby incorporated by reference in its entirety).

As a consequence of this process for triple mutant accumulation/introduction, it was not until relatively recently that HIV virus exhibiting at least three mutations in RT that creates particularly potent resistance to multiple drugs became established. For example, in the United States it was 1992 when the FDA approved the use of combination drug therapy (ddC and AZT). Yet it was not until September of 1995 that clinical trials showed that the combination of AZT with ddC or ddI was more effective than AZT alone. It has only been as a result of the use of combination therapies, where multiple drugs are employed, but in dosage regimes effectively unable to guarantee an adequate 24 hour trough level of the respective drugs, that the particularly problematic strains of multi-resistant HIV virus known in the Western world today have been generated.

Primer Rescue Mutations

The TAM primer rescue mutant originally described comprised various permutations within a group of six drug resistant phenotypes at amino acid positions M41L, D67N, K70R, L210W, T215Y/F and K219Q/E on RT (Larder and Kemp, 1989, Schinazi et al, 2000). Early data pointed to two distinctive mutational pathways for the development of multiple TAM primer rescue mutants, both occurring by unknown factors. The first pathway resulted in an amino acid substitution at codon 210 (210W) and was preferentially associated with mutations at codons 41 (41L; greater than 98%) and 215 (215Y; greater than 94%) as well as a substitution at codon 67 (67N). The second pathway generated a mutation at codon 219 (219K/E), which was preferentially associated with mutations at codons 67 (67N) and 70 (70R) (Yahi et al, 1999). There were therefore two phenotypic patterns: (1) L210W, M41L, T215Y/F, ±D67N, which conferred high levels of viral resistance to AZT and d4T and (2) K219K/E, D67N, K70R, which conferred moderate levels of viral resistance to AZT and d4T.

Marcelin et al (2004) summarized the prevalence of TAM primer rescue-related mutations in virologic failure pateints. Here, 1098 RT sequences were investigated and gave two genotypic patterns as indicated in FIG. 1 and FIG. 2. While different genetic backgrounds may have been present prior to therapy, the sequence and composition of the antiretroviral therapy undertaken when combined with individual differences in pharmacology resulted in viral resistance not only to AZT and d4T but also to other NRTIs. Depending on the mutational pattern present, drug resistance included abacavir (ABC), didanosine (ddI), tenofovir (TNF), lamivudine (3TC), emtricitabine (FTC) and zalcitabine (ddC). Hence, the emergence of primer rescue-related TAMs often plays an important role in the further development of more pronouncedly resistant HIV genotypic patterns. Therefore, one step in preventing multiple nucleoside resistance is to develop a new NRTI with the goal of avoiding the accumulation of primer rescue related TAMs.

Primer rescue-related TAM mutations can evolve concomitantly with other families of escape mutants that typically emerge from combination antiretroviral therapy (otherwise known as cocktail therapy). Today, the cocktail "combivir" (AZT+3TC) is the most frequently used and recommended first line therapy regimen for treatment of naïve HIV patients. It leads, however, to escape mutants which are resistant to both drugs. For example, Miller et al (1998) reported that 3TC-resistant virus with an M184V mutation was selected just 4-12 weeks after initiation of AZT+3TC combination therapy. In time, additional AZT-associated mutations gradually emerged, giving a characteristic genotypic pattern of M184V, M41L, D67N, K70R, L210W, T215Y/F and K219Q/E which is commonly found in treatment experienced patients today. Additional mutations in RT at positions H208, R211, and L214 (Sturmer et al, 2003) and at position G333 (Kemp et al 1998) are reported to be involved in AZT-3TC double resistance and, in particular, to confer an increase in the ability to resist AZT. Therefore, the genotypic context of primer rescue related TAMs has been expanded to include permutations within M184V, M41L, D67N, K70R, H208Y, L210W, R211K, L214F, T215Y/F, K219Q/E and G333E.

Other types of mutations generally seen in treatment experienced patients are V118I and E44D/A. These mutations are strongly correlated to prior exposure to ddI and d4T. In addition, they are often associated with the presence of specific TAM clusters including M41L plus T215Y/F or D67N plus L210W. The result is increased primer rescue-related TAM resistance to the family of thymidine analogues as well as a distinctive role in the dual resistant to AZT+3TC (Montes et al, 2002, Girouard et al, 2003).

The prevalence of drug escape mutants increases as a function of the number of NRTIs used during the course of therapy and forms a pattern of expanded TAMs or NAMs comprising various permutations within M41L, E44D/A, D67N, K70R, V118I, M184V, H208Y, L210W, R211K, L214F, T215Y/F, K219Q/E and G333E. This cluster is also commonly refractory to AZT- and d4T-containing combination therapies and cross-resistant to the entire class of NRTIs.

Significant resistance to thymidine analogues, notably AZT, d4T and TNF, is also found in escape mutants having an amino acid deletion at position 67 (▲67) in the finger region of RT often in association with an amino acid substitution at T69G concomitant with TAM (see Imamichi et al 2000 and 2001). An enhanced RT polymerization activity, which is associated with this particular genotype, is proposed to result in more efficient pyrophosphorolysis-dependent primer excision (described above), leading to the increased resistance Boyer et al, (2004) have also observed that ▲67 concomitant with TAM conferred an increased ability to facilitate primer rescue (excision) viral resistance to AZT and to TNF as compared to TAM alone.

HIV is co-evolving as antiretroviral therapy develops. New mutation phenotypes emerged when double- and triple-nucleoside analogue cocktails were employed in the clinical management of HIV, especially in treatment-naive patients. Complex therapeutic regimens, requiring multiple drugs taken at various times during the day, some with and some without food, are challenging for patients. Failure to comply exactly with these dosing regimes leading to 24 hour trough failures have facilitated the emergence of multiple NRTI resistant HIV viruses, predominantly as a result of virus acquired NAMs or MDRs. For example, a number of groups (e.g. Mas et al, 2000) have observed the emergence of the mutant T69S-XX virus associated with AZT use. This mutant, has a 6-bp insertion in the coding region of its RT between the nucleic acids specifying amino acids 69 and 70. The resulting double amino acid insertion complexes (typically SS, SG or AG insertions) not only led to viral resistance to AZT but also to nearly the entire collection of NRTIs including d4T, 3TC, ddI, ddC and ABC, and TNF. An enhanced pyrophosphorolysis-dependent primer rescue is seen with the T69S+double amino acid insertion, particularly in the presence of TAMs. This phenomenon is typically associated with the "M41L/T215Y" or "M41L/L210W/R211K/L214F/T215Y" resistant phenotypes and plays an important phenotypic role in multiple nucleoside resistance (Meyer et al, 2003).

Another class of MDR has an amino acid substitution at codon Q151M. This mutation is observed at a relatively low frequency in the clinic and often presents together with secondary mutations of A62V, V75I, F77L and F116Y. It confers, however, a significant resistance to nearly the entire class of NRTIs. In addition, it has been observed associated with TAMs, typically the "M41L, L210W and T215Y/F" or "D67N, K70R and K219K/E" genotypes. It emerges in patients that have experienced heavy treatment with AZT/ddI and AZT/ddC combination regimens.

L74V is most frequently selected by ddI monotherapy (Martin et al, 1993) and displays cross-resistance to ABC and 3TC. Its effect on producing viral escapes is dependent upon the presence of other mutations. Resistance surveys suggest that the frequency of L74V is linked significantly with TAM, typically in an M41L, L210W and T215Y/F background (Marcelin et al, 2004) even though the L74V mutation was thought to cause a diminution effect in viral replication and to resensitize AZT-resistant viruses that contain a number of TAMs (St. Clair et al, 1991). A combination of the L74V and M184V mutations in HIV-1 RT is the most frequent pattern associated with resistance to both ABC and ddI (Harrigan et al, 2000 and Miller et al, 2000).

Although high-level resistance to ABC typically requires multiple mutations comprising K65R, L74V, Y115F and M184V, a single mutation, M184V, often emerges first. This mutation, now recognized as a key mutation in the discriminant mechanism of drug escape resistance, confers a moderate decrease in ABC susceptibility (Tisdale et al, 1997). A CNA3005 study in which a total of 562 patients randomly received AZT and 3TC with either ABC or ddI, showed a slow but steady increase in the proportion of patients carrying a TAM in the AZT and 3TC plus ABC arm. By week 48, up to 56% of the patients had at least one primer rescue-related TAM (1×TAM) over and above the rapidly induced M184V mutation (Melby et al, 2001), illustrating the importance of preventing the emergence of primer rescue-related resistance. Similarly, in vitro passage of AZT-resistant virus bearing the genotypic pattern of 67, 70, 215 and 219 under 3TC selective pressure resulted in the selection of the M184V mutation and conferred cross-resistance to ABC (Tisdale et al, 1997). This again highlights the concept that treating the pre-existing of primer rescue-related TAM and preventing the accumulation of primer rescue-related mutants is a pivotal step in avoiding development of multiple nucleoside resistance.

It has become increasingly clear that the K65R mutation quickly appears in a very high proportion of patients who are receiving TNF or ABC. Valer et al (2004) reported that K65R increased in prevalence in their Madrid hospital from <1% between 1997-2000 to 7% in 2003 and 12% in the first 4 months of 2004. The effect of the K65R mutant is exacerbated in the presence of other mutations associated with decreased susceptibility to ABC, 3TC, ddI and ddC (Parikh et al, 2003). Yet the simultaneous appearance of K65R of primer rescue-related TAM genotypes, although rarely occurring, leads to a more profound effect on the primer rescue (excision) of TNF than of AZT (Naeger et al, 2001). TNF was reported to be active against HIV-1 with up to 3×TAMs unless the TAM cluster included an M41L or L210W mutation. Currently it is unclear why TAMs could reverse some of the effects of K65R, which is otherwise thought to impede primer excision mutants with respect to susceptibility to TNF and ABC.

Finally, the T69D mutation was initially identified for its role in causing ddC resistance. It has also been reported to be associated with a decreased response to ddI when it occurs in combination with the T215Y mutation and other of primer rescue-related TAM genotypes.

For many years the WHO and DHHS (US Department of Health and Human Health Service) have recommended first-line antiretroviral therapy on treatment naïve patients consisting of administering d4T or AZT in combination with 3TC plus nevirapine or efavirenz (Guidelines for the Use of Antiviral Retroviral Agents in HIV-1-Infected Adults and Adolescents, Jul. 14, 2003 and Mar. 23, 2004). A substantial number of HIV-infected patients have, however, experienced treatment failure while on their initial highly active antiretroviral therapy (HAART) regimens, suggesting that these patients are already infected with drug escape viruses. Primer rescue-related TAM resistance mutants continue to play a pivotal role in the development of drug resistance. Thus the development of drugs or therapeutic methods that counteract the effect of primer rescue-related TAM resistance mutants could potentiate or prolong the use of existing NRTIs for treating treatment-naïve patients and could also be used to treat the primer rescue-related resistance mutant-carrying HIV infected population in a salvage therapy.

Drug Strategies for Preventing/Inhibiting Primer-Rescue Mutants

Primer rescue and discriminative mutations often appear together in the same mutant genotype, largely due to current therapeutic strategy. A M184V mutation is representative of the family of discriminative mutants. If, however, it occurs in conjunction with primer rescue-related mutants such as M41L, D67N, K70R, L210W, T215Y/F, and K219Q/E, it plays a role in the dual resistance to AZT and 3TC (Miller et al., 1998).

These primer rescue and discriminative resistance phenotypes seem to correlate with different clusters of mutations in RT. For example, AZT-associated mutations comprising various permutations within M41L, E44D/A, D67N, K70R, V118I, M184V, H208Y, L210W, R211K, L214F, T215Y/F, K219Q/E and G333E, an MDR T69S mutation with 6-bp insertions and a ▲67 typically exhibit primer rescue mutant activities. On the other hand, mutations at positions 65, 74, 89, 151, and 184 lead to the ability to discriminate between NRTIs and the respective dNTP counterparts or they may be involved in the repositioning of the primer-template complex.

In the recent article "Designing anti-AIDS drugs targeting the major mechanism of HIV-1 RT resistance to nucleoside analog drugs" (IJBCB 36 (2004) 1706-1715, which is hereby incorporated by reference in its entirety), Sarafianos et al conclude that the primer rescue (excision) mechanism could only occur before RT translocation at the N-site and further conclude that it has become the dominant mechanism of NRTI resistance. In the chapter entitled "Strategies for Inhibition of the Excision Reaction" (see page 1711), they propose three approaches to defeat such a resistance mechanism:

1. use of new antivirals that interfere with the productive binding of ATP (at the P site), presumably by binding at or near the ATP-binding site, thereby blocking the excision reaction without affecting the forward reaction of DNA synthesis.
2. use of compounds that can block DNA synthesis but are somehow resistant to excision, such as borano- or thio-substituted alpha phosphate variants of the current NRTIs. Similarly, variants of the current NRTIs can be engineered to reposition the extended/terminated template/primer in a non-excisable mode, as suggested by the poor excision capacity of the M184I/V mutants induced by 3TC.
3. use of dinucleotide tetraphosphate based inhibitors to provide bi-dentate binding at both N- and P-sites.

Each of these three proposed approaches to preventing primer rescue mechanisms of NRTI resistance is open to criticism for various theoretical shortcomings. For example, in the first approach ATP binding is not required for normal RT functions. Thus, countermeasures based on inhibiting ATP or pyrophosphate binding by competition or blockage will not prevent resistance development because the fitness of the underlying virus will not be compromised by such agents. In other words, resistance mutations will arise at no evolutionary cost. The abundant amount of ATP present in normal lymphocytes also challenges the rationale behind this approach.

In the second proposed approach, it seems likely that borano- or thio-substituted alpha phosphate analogues would select for the discriminative resistant mutants, as has been seen with 3TC and FTC, and produce HIV resistance mutants.

The third proposed approach is limited by the need for pharmacokinetic uptake into the target cell of the large and highly charged tetraphosphate dinucleotide species. This will be a severe pharmaceutical and drug delivery challenge.

It is noteworthy that each of Serafaniano's approaches, including approach 1 which is not antiviral in itself, but presupposes co-administration of a conventional NRTI, is based on variants of the current generation of NRTIs. That is, compounds that lack a 3-hydroxyl function and therefore act as obligate chain terminators.

In contrast to the "classic" NRTIs discussed above (i.e. those lacking a 3'-hydroxy function), Ohrui et al (J Med Chem (2000) 43, 4516-4525, which is hereby incorporated by reference in its entirety) describe 4'-C-ethynyl HIV inhibitors:

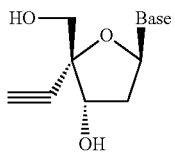

Formula I

These compounds retain the 3'-hydroxy function but nevertheless exhibit activity against HIV-1, including a typical discriminative MDR strain bearing the A62V, V75L, F77L, F116Y and Q151 M mutations. The mechanism of action was postulated to be through affinity to the nucleoside phosphorylating kinase. It was, however, also observed that these compounds may be functioning as DNA chain terminators due to their neopentyl alcohol character and the severe steric hindrance of the vicinal cis 4' substituent, which resulted in a sharply diminished reactivity of the 3'-hydroxy.

Kodama et al (Antimicrob Agents Chemother (2001) 1539-1546, which is hereby incorporated by reference in its entirety) describe a very similar set of compounds bearing a 4'-C-ethynyl group adjacent to the retained 3'-hydroxy function that were assayed in cell culture with additional HIV resistant strains. Since Kodama et al did not prepare the triphosphates of their compounds, they were unable to elucidate the mechanism of action but infer from various circumstantial observations that the compounds are indeed acting as NRTIs. Kodama et al later reported (abstract 388-T, 2003 9th Conference on Retroviruses and Opportunistic Infections, which is hereby incorporated by reference in its entirety) that under the selective pressure of their 4-C-ethynyl nucleoside in vitro, breakthrough resistant HIV bearing T165I and M184V mutations located in the RT catalytic site were found. This mutant phenotype is manifestly a discriminative type of mutation and is heavily cross resistant to 3TC. Steric conflict blocking 4-C-ethynyl nucleoside incorporation was thus implicated. This has been established with the 3TC inhibitory mechanism and therefore almost certainly represents the discriminative resistant mechanism. It therefore seems unlikely that the Kodama compounds will provide guidance in addressing the mutants facilitating primer rescue (ATP or pyrophosphate mediated excision).

Chen et al (Biochemistry (1993) 32:6000-6002, which is hereby incorporated by reference in its entirety) conducted extensive mechanistic investigations on a structurally related series of compounds bearing an azido group at 4':

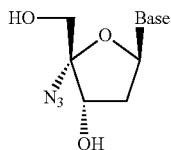

Formula II

Chen demonstrated that RT efficiently incorporates two consecutive 4'-azidothymidine monophosphate nucleotides, which terminates chain elongation. In addition, RT was also able to incorporate a first 4'-azidothymidine monophosphate, followed by a native dNTP and a then a second 4'-azidothymidine nucleotide, which also led to chain termination. Note that both of these mechanisms resulted in a 4'-azidothymidine monophosphate residing at the terminated DNA primer terminus, which is an inhibitory mechanism very reminiscent of the current NRTIs. It was also apparent that the cellular (ie non-viral) polymerases α and β were each able to incorporate a single 4'-azido nucleotide, but not a second, into the nascent chain of the host DNA. These cellular polymerases then allowed the host DNA chain to elongate with further native dNTPs and so permanently incorporated the NRTI nucleotide into host DNA genes. These compounds have not been pursued in humans because misincorporation of non-native nucleotides by cellular enzymes has clear implications in carcinogenesis. Similarly, the pharmaceutical development of the Kodama corresponding 4'-C-ethynyl compounds was stopped, allegedly due to severe toxicity in higher organisms.

EP 341 911 describes an extensive family of 3'-C-hydroxymethyl nucleosides of the formula

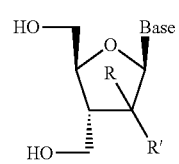

Formula III and proposes their use predominantly against herpesviruses such as CMV, but also against retroviruses. WO92/06201 also discloses a similar set of compounds and indications.

U.S. Pat. No. 5,612,319 (which is hereby incorporated by reference in its entirety) discloses the retroviral activity of 2'-3' dideoxy-3'-C-hydroxymethylcytosine against wild type HIV-1$_{IIIB}$ and the simian equivalent, SIV-1, in an acute cynomolgus monkey model of HIV infection. This publication proposes the use of the compound as a post-exposure prophylaxis agent, especially against needle-stick injuries. Post exposure prophylaxis implies that the active ingredient is immediately administered to people such as medical personnel, who have unwittingly jabbed themselves with a potentially HIV-infected syringe. In order to ensure rapid treatment of an understandably shocked health care professional, a self administered spring-loaded syringe, such as are used for antidotes to chemical and biological warfare, is a preferred administration route.

The intention of post-exposure prophylaxis is to prevent the infection from establishing itself rather than treating an on-going infection. As such, it was intended that treatment was to be carried out for a short time period such as 24-48 hours, using extremely high doses of the compound. This publication states that because of the discrete time period of administration, transient toxicity is acceptable because one is trying to prevent an incurable disease. The post-exposure prophylactic method described in U.S. Pat. No. 5,612,319 has never been tried in humans—indeed to our knowledge 2'-3' dideoxy-3'-C-hydroxymethylcytosine has not been administered to humans at all.

In 1994 when the application granting as U.S. Pat. No. 5,612,319 was filed, multi-resistant HIV as it is known today had not arisen in any cogent form. Today's multi-resistant HIV has primer rescue mutations induced by and accumulated from many years of selective pressure from NRTI therapy. In other words, the HIV and especially the RT existent at the time these patents were granted was structurally and mechanistically very different from today's viruses.

International patent application PCT/EP2005/057196, which was unpublished at the priority date of the present application, discloses the use of 2',3'-dideoxy-3'-hydroxymethylcytosine and prodrugs thereof in the treatment of HIV escape mutants.

It is believed that 2',3'-dideoxy-3'-C-hydroxymethylcytosine is phosphorylated to the corresponding 5'-triphosphate by cellular enzymes. The heavily mutated RT of multiresistant HIV, in particular primer rescue-related mutant RT, incorporates this triphosphate as the 5'-(2',3'-dideoxy-3'-C-hydroxymethylcytosine) monophosphate into the nascent DNA chain.

Conventional NRTIs act as obligate chain terminators, terminating DNA synthesis at the N-site, and are thus susceptible to the above described ATP- or pyrophosphate mediated primer rescue (excision) mechanism unique to mutiresistant HIV. In contrast, 5'-(2',3'-dideoxy-3'-C-hydroxymethylcytosine) monophosphate does not act as an obligate chain terminator, but rather allows an additional residue to be covalently attached to the 3' hydroxymethyl function of the 5'-(2',3'-dideoxy-3'-C-hydroxymethylcytosine) monophosphate. This then promotes the RT to undergo the necessary transformational change to translocate itself into the P-site for the next round of polymerization. Preliminary evidence suggests that this attached terminal residue is a native nucleotide rather than a further 5'-(2',3'-dideoxy-3'-C-hydroxymethyl cytosine) monophosphate.

Importantly, data suggests that the last incorporated, non-2'3'-dideoxy-3'-C-hydroxymethylcytosine nucleotide is not amenable to the further addition of nucleotides by the mutated reverse transcriptase. That is, chain termination appears to occur one base beyond the NRTI of the invention rather than at the NRTI. Furthermore, following the incorporation of 2',3'-dideoxy-3'-hydroxymethylcytosine, the RT appears to successfully translocate to the P-site in order to accept the next incoming nucleotide. This evidence suggests that 2',3'-dideoxy-3'-hydroxymethylcytosine, in conjunction with a primer rescue-related mutated RT, achieves a form of chain termination which is not amenable to ATP- or pyrophosphate induced excision. As a consequence, 2',3'-dideoxy-3'-hydroxymethylcytosine allows effective treatment of HIV infections that are non-responsive to current drug regimes.

The inhibitory mechanism discussed immediately above is thus fundamentally different from the chain termination mechanism of the 4'-substituted nucleosides of Chen et al (see above), which allows several nucleotides to be incorporated after the incorporated 4-substituted compound. Firstly, the Chen mechanism dramatically enhances the risk of "readthrough." That is, the DNA polymerase continues to follow the coding strand and continues to add the coded residues to the normal stop codon, thereby misincorporating the abnormal nucleoside within the DNA strand. Antiviral efficacy can be lost, however, when a viral DNA strand is constructed by the viral polymerase (i.e. RT) since the readthrough construct may still be viable, notwithstanding the misincorporated 4'-substituted nucleoside. More importantly, if the 4'-substituted nucleoside is readthrough by a cellular (i.e. host) polymerase, as Chen describes, the resulting construct thereafter represents a teratogen and dramatically increases the risk of cellular damage and cancer.

The Chen compounds additionally require the addition of a second 4'-substituted nucleotide, either immediately adjacent to the first mis-incorporated 4'-substituted nucleotide (i.e. X—X) or interspersed by one native nucleotide (i.e. X—N—X). In practice this means that the nucleotide at the last position of the primer terminus is the non-native (i.e. drug) nucleotide. This is an analogous situation to the case of classic NRTIs (i.e. those lacking a 3-hydroxy group) chain termination. Here, the NRTI nucleotide also resides at the last position of the primer terminus where, as discussed above, it is susceptible to ATP or pyrophosphate mediated excision.

Multiple units of the Chen 4'-substituted nucleotide are needed in order for it to work as an efficient RT inhibitor. As a consequence, the drug's effectiveness depends on the sequence of the reading strand. For example, if the Chen compound is a thymidine analogue it will have the best affinity if the reading strand has an AA or A-N-A sequence. Here, the drug would be efficient and effective in terminating DNA synthesis. But if the reading strand's sequence does not contain abundant recitals of the AA or A-N-A sequence, the Chen drug will be less able to terminate DNA synthesis, at a given concentration. Since an AA doublet or an A-N-A triplet is far less common in the genome than a singlet A, the Chen drug will be far less efficient than other NRTIs that do not have a multiple unit requirement.

Mauldin et al *Bioorganic and Medicinal Chemistry* 1998 6:577-585 discloses a number of 2',3'-dideoxy-3'-hydroxymethylcytosine prodrugs. Of particular note is the fact that the authors found that prodrugs involving substituents at the alcohol positions resulted in a decrease in antiviral activity in virtually all of their assays.

It is an object of the present invention to provide novel prodrugs of 2',3'-dideoxy-3'-hydroxymethylcytosine, of use in the treatment of HIV, and in particular in the treatment of HIV escape mutants.

BRIEF DESCRIPTION OF THE INVENTION

In accordance with a first aspect of the invention, there are provided novel compounds of the formula I:

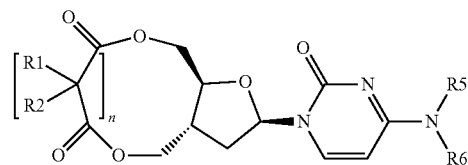

wherein:
$R^1$ is independently H, —$OR^3$, —$NHR^4$; $C_1$-$C_4$ alkyl;
or, when n is 2, adjacent $R^1$ together define an olefinic bond;
$R^2$ is H;
or when the gem $R^1$ is $C_1$-$C_4$ alkyl, that $R^2$ may also be $C_1$-$C_4$ alkyl;
or when the gem $R^1$ is —$OR^3$, that $R^2$ may also be —C(=O)OH or a pharmaceutically acceptable ester thereof;
$R^3$ is independently H, or a pharmaceutically acceptable ester thereof;
$R^4$ is independently H or a pharmaceutically acceptable amide thereof;
$R^5$ is H, —C(=O)$R^7$, or an amide-bound L-amino acid residue;
$R^6$ is H;
or $R^5$ and $R^6$ together define the imine =$CR^8R^{8'}$;
$R^7$ is $C_1$-$C_6$ alkyl, $C_0$-$C_3$alkylcycyl;
$R^8$ and $R^{8'}$ are independently H, $C_1$-$C_6$ alkyl, $C_0$-$C_3$alkylcycyl;
or $R^8$ is H and $R^{8'}$ is —$NR^9R^{9'}$;
$R^9$ and $R^{9'}$ are independently H, $C_1$-$C_6$ alkyl, $C_0$-$C_3$alkylcycyl;

or R⁹ and R⁹' together with the N atom to which they are attached define a saturated 5 or 6 membered ring;
n is 1, 2 or 3;
and pharmaceutically acceptable salts thereof.

According to one embodiment of the invention, n is 1 and the compounds have the general formula:

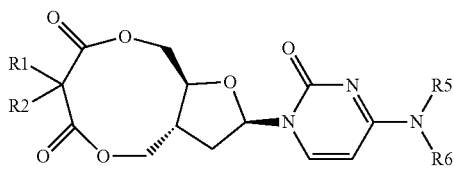

Favoured variants for R1:R2 in this embodiment include H:H, H:OH or a pharmaceutically acceptable ester thereof, and Me:Me. Particularly favoured variants of this embodiment have H as $R^5$ and $R^6$.

An alternative embodiment of the invention has n=2, thereby producing compounds of the general formula:

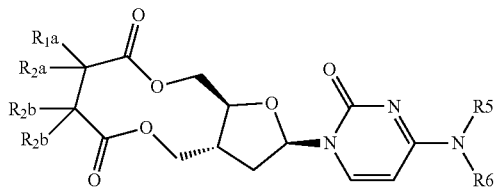

In this embodiment favoured variants for $R^1a:R^1b:R^2a:R^2b$ include
H:H:H:H
H:H:H:OH or a pharmaceutically acceptable ester thereof.
H:H:H:NH₂ or a pharmaceutically acceptable amide thereof
H:OH or a pharmaceutically acceptable ester thereof: H:H
H:NH₂ or a pharmaceutically acceptable amide thereof: H:H
Me:Me:H:H
H:H:Me:Me
H:OH:H:OH
H:C═C:H
Particularly favoured variants of this embodiment have H as $R^5$ and $R^6$.

A further embodiment of the invention has n equal to 3, with the general formula:

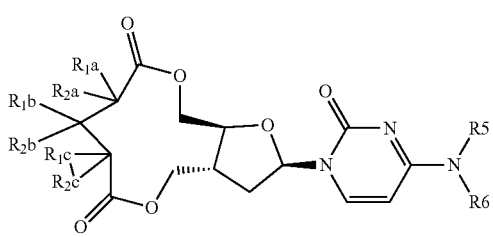

Favoured variants of $R^1a:R^2a:R^2a:R^2b:R^1c:R^2c$ include
H:H:H:H:H:H
H:H:Me:Me:H:H
H:H:OH:H:H:H
H:H:OH:COOH:H:H
H:H:H:H:H:NH₂
or a pharmaceutically acceptable ester or amide thereof.

Particularly favoured variants of this embodiment have H as $R^5$ and $R^6$.

Certain embodiments of the invention have a modified base, ie $R^5$ and/or $R^6$ are other than hydrogen. One such embodiment are imines, wherein $R^5$ and $R^6$ together define the imine ═$CR^8R^{8'}$. Typically $R^8$ and $R^{8'}$ will each be the same alkyl group, but asymmetric R8/R8' variants are also within the scope of the invention. Representative imines within this embodiment include:
═CHN(CH₃)₂
═CHN(ipr)₂
═CHN(pr)₂
Alternatively $R^8$ and $R^{8'}$ can together define a cyclic group such as pyrrolidine, piperidine, piperazine, N-methyl piperazine or morpholine, Representative imines thus include:
═CHN(CH₂)₄
═CHN(CH₂)₅
═CHN(CH₂)₆
═CHN(CH₂CH₂)₂O
It is currently preferred that $R^5$ and $R^6$ are H.
Other embodiments of the invention wherein $R^5$ and $R^6$ are other than H include amides, such as L-amino acid amides, such as Ile, Val, Leu or Phe amides. Alternative amides include alkyl amides such as $C_1$-$C_6$ alkyl amides, for example those wherein $R^5$ is C(═O)CH₃, C(═O)CH₂CH₃ or C(═O)C(CH₃)₃. Other amides include C(═O)$C_0$-$C_3$alkylaryl amides, such as C(═O)Ph or C(═O)Bz.

Currently preferred embodiments include the compounds of formula I denoted
2-(4-amino-2-oxo-2H-pyrimidin-1-yl)-octahydro-1,5,10-trioxacyclopenta-cyclodecene-6,9-dione; or
2-(4-amino-2-oxo-2H-pyrimidin-1-yl)-octahydro-1,5,11-trioxa-cyclopentacycloundecene-6,10-dione;
or a pharmaceutically acceptable salt thereof. These compound release innocuous by-products upon hydrolysis in vivo, such as succinic or glutaric acid.

Although not wishing to be bound by theory it is believed that the compounds of the invention, or active metabolites thereof, are active against the reverse transcriptase of retroviruses such as HIV-1, HIV-2, HTLV and SIV.

Accordingly a further aspect of the invention provides methods for the prophylaxis or treatment of retrovirus infections in humans or animals comprising the administration of a compound of the formula I, or a pharmaceutically acceptable salt thereof. Typically the administration is oral.

A further aspect of the invention provides the use of compounds of the formula I, or a pharmaceutically acceptable salt thereof in the manufacture of a medicament for the treatment or prophylaxis of retroviral infections in humans or animals. Typically the medicament is in a form adapted for oral administration.

Another embodiment of the invention provides a method for inhibiting the emergence or propagation of HIV primer rescue mutants that are able to remove a chain-terminating NRTI nucleotide incorporated into an HIV primer/template complex where the removal is effected by an ATP-dependent or pyrophosphate dependent excision mechanism. The method comprises the simultaneous or sequential administration to an individual infected with HIV an effective amount of the compound of the invention and at least one chain terminator NRTI which induces primer rescue mutants.

Conventional NRTIs act as obligate chain terminators, terminating DNA synthesis at the N-site, and are thus susceptible to the above described ATP- or pyrophosphate mediated primer rescue (excision) mechanism unique to mutiresistant HIV. In contrast, preliminary evidence suggests that the compounds of the invention do not act as an obligate chain terminator, but rather allows an additional residue to be covalently attached to the 3' hydroxymethyl function of the 5'-(2',3'-dideoxy-3'-C-hydroxymethylcytosine) monophosphate. This then promotes the RT to undergo the necessary transformational change to translocate itself into the P-site for the next round of polymerization. Preliminary evidence based on the sequence of the template presented below suggests that this attached terminal residue is a native nucleotide.

The multiresistant HIV typically able to be treated or prevented according to the invention will typically have an RT bearing a genetic pattern comprising at least one of
 (a) M41, ±D67, L210 and T215;
 (b) D67, K70 and K219;
 (c) T69S-XX or
 (d) ▲67
where XX represents an addition to the RT sequence of any two natural amino acids and ▲67 represent the amino acid deletion at codon 67.

Although the above 4 genetic patterns are believed to represent the essential basis of the excision drug escape phenotype, t will be apparent that the mutants treated or prevented by the use of the invention will typically comprise additional mutations in the RT gene and elsewhere, often at least three mutations in the RT gene.

Generally, but not exclusively, the cluster M41, ±D67, L210 and T215 will often comprise M41L, ±D67N, L210W and T215Y or T215F.

Optionally, the clusters immediately above may further comprises at least one further mutation at position E44, K70, V118, H208, R211K, L214, K219 or G333.

The clusters immediately above may further comprise at least one additional mutation at position ▲67, T69, E203, L210, D218, H221, D223 or L228.

Generally, but not exclusively, the cluster D67, K70 and K219 comprises D67N, K70R and K219Q or K219E.

Optionally, the cluster D67, K70 and K219 may further comprise at least one additional mutation at position M41, E44, V118, H208, L210, R211K, L214, T215, or G333.

In addition, the cluster D67, K70 and K219 optionally further comprises at least one additional mutation at position ▲67, T69, E203, L210, D218, H221, D223 or L228.

Generally, but not exclusively, the cluster T69S-XX may further comprise at least one additional mutation at position M41, E44, D67, K70, V118, H208, L210, R211K, L214, T215, K219 or G333.

Optionally, the cluster T69S-XX may further comprise at least one additional mutation at position ▲67, T69, E203, L210, D218, H221, D223 or L228.

Generally, but not exclusively, the cluster ▲67 may further comprise at least one additional mutation at position M41, E44, D67, K70, V118, H208, L210, R211K, L214, T215, K219 or G333.

Optionally, the cluster ▲67 may further comprise at least one additional mutation at position T69, T69S+XX, E203, L210, D218, H221, D223 or L228.

Optionally, the reverse transcriptase may further bear at least one discriminative mutation at position K65, L74, M184 or Q151, especially
K65R, L74V or M184V or Q151M.

Typically, the cluster of discriminative mutants may be linked with at least one additional mutation at position A62, V75, F77, Y115 or F116.

Among the HIV strains able to be treated by the invention are multiresistant HIV strains whose RT has mutations that encourage ATP- or pyrophosphate-mediated primer rescue (excision) of chain terminating NRTI nucleotides and which has arisen within the patient as a result of previous HIV-treatment with at least one antiviral selected from zudovudine (AZT, ZDV), stavudine (d4T), zalcitabine (ddC), didanosine (ddI), abacavir, (ABC), lamivudine (3TC), emtricitabine (FTC), adefovir (ADV), entacavir (BMS 200475) alovudine (FLT), tenofovir disoproxil fumarate (TNF), amdoxavir (DAPD), D-d4FC (DPC-817), -dOTC (SPD754), SPD-756, racivir, D-FDOC or GS7340.

Alternatively, the HIV strains are those found in patients who have received such a resistant or multiresistant HIV strain directly or indirectly from another individual who had themselves induced a resistant or multiresistant HIV strain by sustained treatment with at least one antiviral from the above list of NRTI antivirals. Frequently the mulitresistant HIV strains contain at least three mutations in the viral RT as compared to wildtype.

It will thus be apparent that the methods and composition of the invention may be used as an add-on to current antiretroviral therapies, such as HAART, or in some cases as a rescue or salvage therapy. This will typically be the case where the multiresistant HIV has been induced in the actual patient by that patient's earlier antiretroviral drug treatment history. Alternatively, the methods and compositions of the invention will constitute a first line therapy, typically in patients whose primary HIV infection occurred with an already-mutated multiresistant strain. The following antiviral drugs often induce such multiresistant HIV strains having RT primer rescue mutations which encourage ATP- or pyrophosphate-mediated excision of chain terminating NRTI nucleotides:

zudovudine, lamivudine or the combined dosage forms Combivir or Trizivir;
lamivudine, abacavir or the combined dosage form Epzicom;
tenofovir, emtricitabine or the combined dosage form Truvada.

While these drugs frequently induce such multiresistant HIV strains, this drug list is not exclusive.

It is therefore apparent that the compound of the invention is administered in order to prevent the emergence of one or more multiresistant HIV strains having RT primer rescue mutations that encourage ATP- or pyrophosphate-mediated excision of chain terminating NRTI nucleotides. This prevention occurs even when NTRI drugs which induce such mutations are administered concomitantly.

A third aspect of the invention provides a pharmaceutical composition in unit dosage form comprising the compound of formula I and at least one chain terminator NRTI, where upon sustained dosing with the NRTI induces, HIV RT primer rescue mutations which encourage ATP-dependent or pyrophosphate-dependent excision of incorporated NRTI monophosphate from the 3'-terminus of the primer/template complex and allows resumption of DNA synthesis.

Preferred embodiments of the pharmaceutical composition of the invention and the method of the invention include those where the NRTI is selected from zudovudine (AZT, ZDV), stavudine (d4T), zalcitabine (ddC), didanosine (ddI), abacavir, (ABC), lamivudine (3TC), emtricitabine (FTC), adefovir (ADV), entacavir (BMS 200475), alovudine (FLT), tenofovir disoproxil fumarate (TNF), amdoxavir (DAPD), D-d4FC (DPC-817), -dOTC (SPD754), SPD-756, racivir, D-FDOC or GS7340 and combinations thereof.

Particularly preferred embodiments include those where the NRTI is selected from: zidovudine, stavudine, didanosine, lamivudine, abacavir, tenofovir, emtricitabine or combinations thereof.

Experience with HIV drugs, and HIV reverse transcriptase inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$ is essential to slow down the development of drug escape mutants.

The compounds of the invention are typically administered to the patient at a dose commensurate with the expectation of a sustained and protracted antiretroviral treatment. The treatment regimen thus aims to ensure a defined drug level, yet to avoid toxicity, although the use of compounds of formula I in a high-dose, acute, post-exposure prophylaxis treatment can tolerate some transient toxicity is acceptable. The compounds of formula I are typically administered in ranges of 1-25 mg/kg/day, preferably less than 10 mg/kg/day, preferably in the range of 0.05-0.5 mg/kg/day. The appropriate dosage will depend upon the indications and the patient, and is readily determined by conventional animal drug metabolism and pharmacokinetics (DMPK) or clinical trials and in silico prediction software.

The unit dosage pharmaceutical compositions of the invention have corresponding amounts of the compound of formula I, typically scaled for a 60 kg or 75 kg adult, and are optionally divided once, twice or three times for a QD, BID or TID dosage regime. If the therapeutic dose is in the range of 0.05-0.5 mg/kg/day, then a clinical QD dose per person per day would be 3 mg-30 mg for a 60 kg adult or 3.75-37.5 mg for a 75 kg adult. Dosage and regiment restrictions of the additional conventional NRTI in the combined dosage unit pharmaceutical composition aspect of the invention may necessitate QD, BID or TID dosing.

The current invention includes pharmaceutically acceptable salts such as salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate. Also included are the salts of organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate. The acceptable salts also include those from inorganic acids such as hydrochloride, hydrobromide, hydroiodide, sulphate, bisulphate, hemisulphate, thiocyanate, persulphate, phosphoric and sulphonic acids.

The current invention extends to active agents that are hydrates, solvates, complexes and other physical forms releasing the compound of formula I.

While it is possible for the active agent to be administered alone, it is preferable to present it as part of a pharmaceutical formulation. Such a formulation will comprise the compound of formula I active agent together with one or more acceptable carriers/excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration. Preferably the formulation is an orally administered formulation. The formulations may conveniently be presented in unit dosage form, e.g. tablets and sustained release capsules, and may be prepared by any methods well known in the art of pharmacy.

Such well known methods include the step of bringing the compound of formula I active agent into association with the carrier. In general, the formulations are prepared by uniformly and intimately bringing the active agent into association with liquid carriers or finely divided solid carriers or both, and then shaping the product, if necessary. The invention extends to methods for preparing a pharmaceutical composition comprising bringing a compound of formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient is in a salt form, then it is often preferred to use excipients which are non-basic in nature, i.e. either acidic or neutral.

The formulations for oral administration of the present invention may be presented as discrete units such as capsules, cachets or tablets, each containing a predetermined amount of the active agent. Alternatively they can be presented as a powder or granules; as a solution or a suspension of the active agent in an aqueous liquid or a non-aqueous liquid, or as an oil-in-water liquid emulsion or a water-in-oil liquid emulsion, as a bolus, etc.

With regard to compositions for oral administration (e.g. tablets and capsules), the term "suitable carrier" includes vehicles such as common excipients, for example binding agents such as syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredient. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

'$C_1$-$C_6$alkyl' (also abbreviated as $C_1$-$C_6$alk, or used in compound expressions such as $C_1$-$C_6$alkyloxy etc) as applied herein is meant to include straight and branched chain aliphatic carbon chains such as methyl, ethyl, n-propyl, isopropyl, n-butyl, isobutyl, t-butyl, pentyl, isopentyl, hexyl, heptyl and any simple isomers thereof. The alkyl group may have an unsaturated bond. Additionally, any C atom in $C_1$-$C_6$alkyl may optionally be substituted by one, two or where valency permits three halogens and/or substituted or the alkylene chain interrupted by a heteroatom S, O, NH. If the heteroatom is located at a chain terminus then it is appropriately substituted with one or 2 hydrogen atoms. $C_1$-$C_n$alkyl has the corresponding meaning to $C_1$-$C_6$alkyl adjusted as necessary for the carbon number.

'$C_0$-$C_3$alkylaryl' as applied herein is meant to include an aryl moiety such as a phenyl, naphthyl or phenyl fused to a $C_3$-$C_7$cycloalkyl for example indanyl, which aryl is directly bonded (i.e. $C_0$) or through an intermediate methyl, ethyl, propyl, or isopropyl group as defined for $C_1$-$C_0$alkylene above. Unless otherwise indicated the aryl and/or its fused cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxyC_1$-$C_6$alkyl, $C_1$-$C_6$alkanoyl, amino, azido, oxo, mercapto, nitro $C_0$-$C_3$alkylcarbocyclyl, $C_0$-$C_3$alkylheterocyclyl. "Aryl" has the corresponding meaning, i.e. where the $C_0$-$C_3$alkyl linkage is absent.

'$C_0$-$C_3$alkylC$_3$C$_7$cycloalkyl' as applied herein is meant to include a $C_3$-$C_7$cycloalkyl group such as cyclopropyl, cyclobutyl, cyclopentyl, cyclohexyl or cycloheptyl, which cycloalkyl is directly bonded (i.e. $C_0$alkyl) or through an intermediate methyl, ethyl or proyl group as defined for $C_1$-$C_3$alkylene above. The cycloalkyl group may contain an unsaturated bond. Unless otherwise indicated the cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxyC_1$-$C_6$alkyl, $C_1$-$C_6$alkanoyl, amino, azido, oxo, mercapto, nitro $C_0$-$C_3$alkylcarbocyclyl, $C_0$-$C_3$alkylheterocyclyl.

'$C_0$-$C_3$alkylcarbocyclyl' as applied herein is meant to include $C_0$-$C_3$alkylaryl and $C_0$-$C_3$alkylC$_3$-$C_7$cycloalkyl. Unless otherwise indicated the aryl or cycloalkyl group is optionally substituted with 1-3 substituents selected from halo, hydroxy, nitro, cyano, carboxy, $C_1$-$C_6$alkyl, $C_1$-$C_6$alkoxy, $C_1$-$C_6$alkoxyC_1$-$C_6$alkyl, $C_1$-$C_6$alkanoyl, amino, azido, oxo, mercapto, nitro, $C_0$-$C_3$alkylcarbocyclyl and/or $C_0$-$C_3$alkylheterocyclyl. "Carbocyclyl" has the corresponding meaning, i.e. where the $C_0$-$C_3$alkyl linkage is absent '$C_0$-$C_3$alkylheterocycylyl' as applied herein is meant to include a monocyclic, saturated or unsaturated, heteroatom-containing ring such as piperidinyl, morpholinyl, piperazinyl, pyrazolyl, imidazolyl, oxazolyl, isoxazolyl, thiazinolyl, isothiazinolyl, thiazolyl, oxadiazolyl, 1,2,3-triazolyl, 1,2,4-triazolyl, tetrazolyl, furanyl, thienyl, pyridyl, pyrimidyl, pyridazinyl, pyrazolyl, or any of such groups fused to a phenyl ring, such as quinolinyl, benzimidazolyl, benzoxazolyl, benzisoxazolyl, benzothiazinolyl, benzisothiazinolyl, benzothiazolyl, benzoxadiazolyl, benzo-1,2,3-triazolyl, benzo-1,2,4-triazolyl, benzotetrazolyl, benzofuranyl, benzothienyl, benzopyridyl, benzopyrimidyl, benzopyridazinyl, benzopyrazolyl etc, which ring is bonded directly i.e. ($C_0$), or through an intermediate methyl, ethyl, propyl, or isopropyl group as defined for $C_1$-$C_3$alkylene above. Any such non-saturated rings having an aromatic character may be referred to as heteroaryl herein. Unless otherwise indicated the hetero ring and/or its fused phenyl moeity is optionally substituted with 1-3 substituents selected from halo, hydroxy, nitro, cyano, carboxy, $C_1$-$C_6$alkyl, $C_1$-$C_6$alkoxy, $C_1$-$C_6$alkoxyC_1$-$C_6$alkyl, $C_1$-$C_6$alkanoyl, amino, azido, oxo, mercapto, nitro, $C_0$-$C_3$alkylcarbocyclyl, $C_0$-$C_3$alkylheterocyclyl. "Heterocyclyl" and "Heteroaryl" have the corresponding meaning, i.e. where the $C_0$-$C_3$alkyl linkage is absent.

Typically heterocycyl and carbocyclyl moieties within the scope of the above definitions are thus a monocyclic ring with 5 or especially 6 ring atoms, or a bicyclic ring structure comprising a 6 membered ring fused to a 4, 5 or 6 membered ring.

Typical such groups include $C_3$-$C_8$cycloalkyl, phenyl, benzyl, tetrahydronaphthyl, indenyl, indanyl, heterocyclyl such as from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, any of which may be optionally substituted as defined herein.

The saturated heterocycle moiety thus includes radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidinylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione, whereas the unsaturated heterocycle include radicals with an aromatic character such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl. In each case the heterocycle may be condensed with a phenyl ring to form a bicyclic ring system.

The compounds of formula I include certain pharmaceutically acceptable esters or amides. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); amino acid esters (for example, L-valyl or L-isoleucyl); and mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above.

Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like.

Alternative aryl or heteroaryl esters include benzoyl, pyridylmethyloyl and the like any of which may be substituted, as defined in carbocyclyl above. Preferred pharmaceutically acceptable esters include aliphatic L-amino acid esters such as leucyl, isoleucyl and especially valyl. Additional preferred amino acid esters include the 2-O-AA-$C_3$-$C_{22}$ fatty acid esters described in WO99 09031, where AA is an aliphatic amino acid ester, especially those derived from L-lactic acid and L-valyl.

Pharmaceutically acceptable amides include those derived from $C_1$-$C_{22}$ branched or straight chain aminoalkyl optionally including 1 to 3 unsaturations and/or optionally substituted with the substituents defined in carbocycylyl above, or anilines or benzylamines. Preferred amides include those formed from reaction of the amine with a $C_1$-$C_4$ straight or branched chain alkanoic acid. Other pharmaceutically acceptable amides of amine functions correspond to the amides of the carboxylic acids preferred for the esters indicated above.

Synthesis

The compounds of the invention are typically synthesized from a differentially protected bis-4,5-hydroxymethyltetrahyrdofuran derivative prepared analogously to Svansson L. et al. in J. Org. Chem. (1991) Vol 56: 2993-2997, as outlined in Scheme 1:

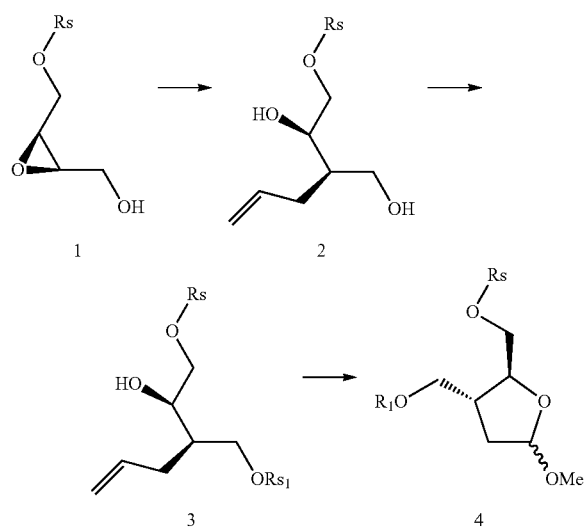

In Scheme 1, chiral epoxy alcohol 1 is readily prepared using Sharpless oxidation as shown in J Org Chem 1987, 52, 2596. Rs is a conventional hydroxyl protecting group such as those discussed below, for example para-bromobenzyl. Epoxy alcohol 1 is regioselectively alkylated at C-3, for example with allyl magnesium bromide in dimethyl ether at −50 degrees C. Chromatography, for example with silica gel, separates the desired isomer 2, optionally after a differentiation step in which the vicinyl hydroxyls of the non-desired regioisomer are cleaved with an oxidizing agent such as sodium periodate. The primary hydroxyl group in 2 is protected with a further hydroxyl protecting group, for example benzoylation with benzoyl chloride in pyridine at 0 degrees C. producing a differentially protected 3. Cis-hydroxylation of the olefinic bond using a catalytic amount of osmium tetroxide and N-methylmorpholine N-oxide as reoxidant, as described in Tet. Lett 1976 17 1973 yields the corresponding di-alcohol which in turn is cleaved with an oxidizing agent such as sodium periodate in an organic solvent such aqueous tetrahydrofuran. The thus-produced unstable furanose is deblocked with a alcohol/acid such as 0.5% w/w methanol in hydrochloric acid to give the differentially protected bis-4,5-hydroxymethyltetrahydrofuran intermediate 4.

It may be desirable to manipulate the protecting groups Rs and Rs1 (ie to remove and reprotect with a further hydroxyl protecting group, thereby to optimize the ease of selective removal of a selected one of the protecting groups and not the other in later steps. The differential protecting groups in 4 are thus selected so as to enable selective removal of one such protecting group and acylation of the thus-exposed hydroxyl function as shown below in Schemes 2 and 3. Many such pairs of differentially selectable hydroxyl protecting groups are known, for example the O-protecting groups disclosed in Greene, "Protective Groups In Organic Synthesis," (John Wiley & Sons, New York (1981)).

Hydroxy-protecting groups thus comprise ethers such as methyl ether or substituted methyl ethers, for example, methoxymethyl (MOM), benzyloxymethyl, t-butoxymethyl, 2-methoxyethoxymethyl (MEM), 2,2,2-trichloroethoxymethyl, bis(2-chloroethoxy)methyl, 2-(trimethylsilyl)ethoxymethyl, terohydropyranyl (THP), 3-bromotetrahydropyranyl, tetrahydrothiopyranyl, 4-methoxytetrahydropyranyl, 4-methoxytetrahydrothiopyranyl S,S dixido, tetrahydrofuranyl and tetrahydrothiofuranyl. Ethyl ethers include 1-ethoxyethyl, 1-methyl-1-methoxyethyl, 1-(isopropoxy)ethyl, 2,2,2-trichloroethyl and 2-(phenylselenyl)ethyl. Other ethers include t-butyl, allyl, cinnamyl, p-chlorophenyl and benzyl ethers such as unsubstituted benzyl, p-methoxybenzyl, o-nitrobenzyl, p-nitrobenzyl, p-halobenzyl and p-cyanobenzyl. Other ethers include 3-methyl-2-picolyl N-oxido, diphenylmethyl, 5-dibenzosuberyl, triphenylmethyl, alpha naphthyldiphenylmethyl, p-methoxyphenyldiphenylmethyl, p(p'-bromophenacyloxy)phenyldiphenylmethyl, 9-anthryl, 9-(9-phenyl)xanthenyl, 9-(9-phenyl-10-oxo)anthryl(tritylone) and benzisothiazolyl S,S dioxodo. Silyl ethers include trimethylsilyl (TMS), triethylsilyl, isopropyldimethylsilyl, t-butyldimethylsilyl (TBDMS), (triphenylmethyl)dimethylsilyl, t-butyldiphenylsilyl, methyldiisopropylsilyl, methyldi-t-butylsilyl, tribenzylsilyl, tri-p-xylylsilyl, triisopropylsilyl and tripenylsilyl. Alternative hydroxyl protecting groups include esters, such as the formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, p-(P)-phenylacetate, 3-phenylpropionate, 3-benzoylpropionate, isobutyrate, monosuccinate, 4-oxopenatanoate (levinulate), pivaloate, adamantoate, crotonate, 4-methoxycrotonate, (E)-2-methyl-2-butenoate (tigloate) and benzoates such as the unsubstituted, or o-(dibromomethyl)-, o-(methoxycarbonyl)-, p-phenyl-, 2,4,6-trimethyl-(mesitate) or p-(P)-benzoates, or alpha-naphthoate. Carbonate hydroxyl protecting groups include the methyl, ethyl, 2,2,2-trichloroethyl, isobutyl, vinyl, allyl, cinnamyl, p-nitrophenyl, benzyls such as the unsubstituted, p-methoxy-, 3,4-dimethoxy-, o-nitro- or p-nitrobenzyls, or S-benzyl thiocarbonate. Miscellaneous hydroxyl protecting groups include N-phenylcarbamate, N-imidazolylcarbamate, borate, nitrate, N,N,N,N-tetramethylphosphorodiamidate and 2,4-dinitrophenylsulfenate. Greene provides extensive reactivity charts to facilitate is selecting complementary pairs of differential protecting groups.

Representative hydroxyl protecting groups include those in the examples, and ethers such as t-butyl and other lower alkyl ethers, such as isopropyl, ethyl and especially methyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The differentially protected bis-4,5 hydroxmethyltetrahydrofuran 4 is then condensed with a silylated, optionally N-protected 4-amino-pyrimidinone, as shown in Scheme 2, followed by acylation and cyclisation. Alternatively 4 is first bicyclised and then condensed, as shown in Scheme 3.

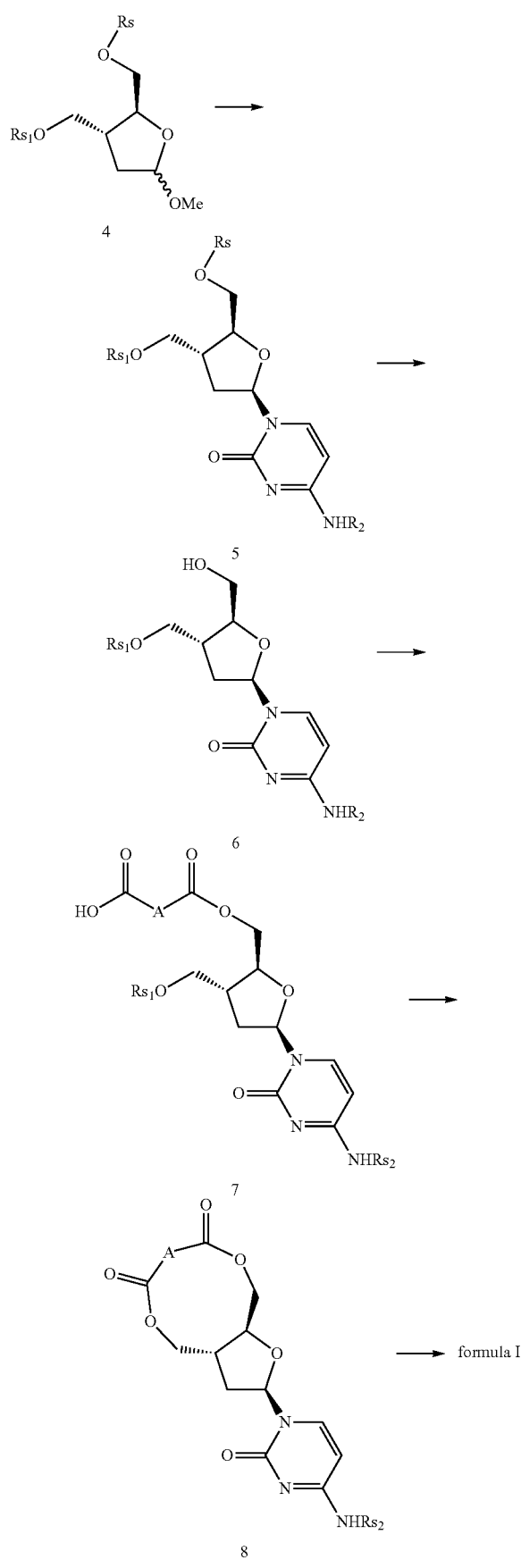

Scheme 2 shows a Vorbrüggen condensation (Chem. Ber. 1981, 114, 1234) of the differentially protected intermediate 4 with silylated 4-amino-pyrimidin-2-one, wherein the 4-amino function is optionally protected with a convention amino protecting group as shown in Greene, "Protective Groups In Organic Synthesis," (John Wiley & Sons, New York (1981)). Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted bensyloxycarbonyls, and 9-fluorenylmethyloxycarbonyl (Fmoc); 3) aliphatic carbamate groups such as tertbutyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. The amino protecting group is of course selected such that its deprotection conditions harmonise with the removal sequence of the differential hydroxyl protecting groups. Alternatively $Rs^2$ is a synthon for the amides and imines defined for $R^5$ and $R^6$. In many cases no protecting group at all is required for the 4-amino function and thus $Rs^2$ is H.

As is conventional in Vorbrüggen condensation, the reaction mixture contains TBDMSOTf and $CH_2Cl_2$ and the desired isomer 5 is separated with chromatography, for example HPLC. One of the hydroxyl protecting groups in 5 is then selectively removed to uncover the hydroxyl function. In scheme 2, compound 6, it is Rs which is removed first, and the differential pair of hydroxyl protecting groups can thus for example be TBDP (tert-butyl-silanyl) selectively removed with TBAF in tetrahydrofuran for Rs, and MMTR (4-methoxy-phenyl-diphenylmethy) subsequently removed with acetic acid for $Rs^1$. However it is readily apparent that other permutations of protecting groups will achieve the same goal. Greene provides extensive reactivity charts over diverse protecting groups to facilitate such selection. Additionally, swapping the positions of Rs and $Rs^1$ by the appropriate manipulation of 4 will produce an intermediate in which the 4-hydroxymethyl function is unmasked and acylated first.

The unmasked hydroxyl function in 6 is acylated with an activated, ωω-dicarboxylic acid HOOC-A-COOH, where A corresponds to —$(CR^1R^2)_n$— as defined above to yield 7. In the event that $R^1$ or $R^2$ contain a potentially reactive group such as OH, $NH_2$ or COOH, these are conventionally protected as described in Greene ibid.

The activated acid used in the acylation may comprise e.g, the acid halide, acid anhydride, activated acid ester or the acid in the presence of coupling reagent, for example dicyclohexylcarbodiimide. Representative activated acid derivatives include the acid chloride, anhydrides derived from alkoxycarbonyl halides such as isobutyloxycarbonylchloride and the like, N-hydroxysuccinamide derived esters, N-hydroxyphthalimide derived esters, N-hydroxy-5-norbornene-2,3-dicarboxamide derived esters, 2,4,5-trichlorophenol derived esters and the like. Further activated acids include those of the formula HCOOHACOOX where X for example is $COCH_3$, $COCH_2CH_3$ or $COCF_3$ or benzotriazole.

Protecting group $Rs^1$ in Compound 7 is then removed to free up the 4 hydroxymethyl group of 8 in preparation for cyclisation of the second ring of the bicyclic tetrahydrofuran ring system. This proceeds via acylation as described in principle above.

Group $Rs^2$ of Compound 8, is then manipulated to produce the compounds of formula 1, as needed. For example an amino protecting group as $Rs^2$ can be removed to yield the free amine at $R^5$ & $R^6$ and/or the amine function converted to an amide or imine as described below.

An alternative synthesis scheme for the compounds of formula 1 is shown in FIG. 3:

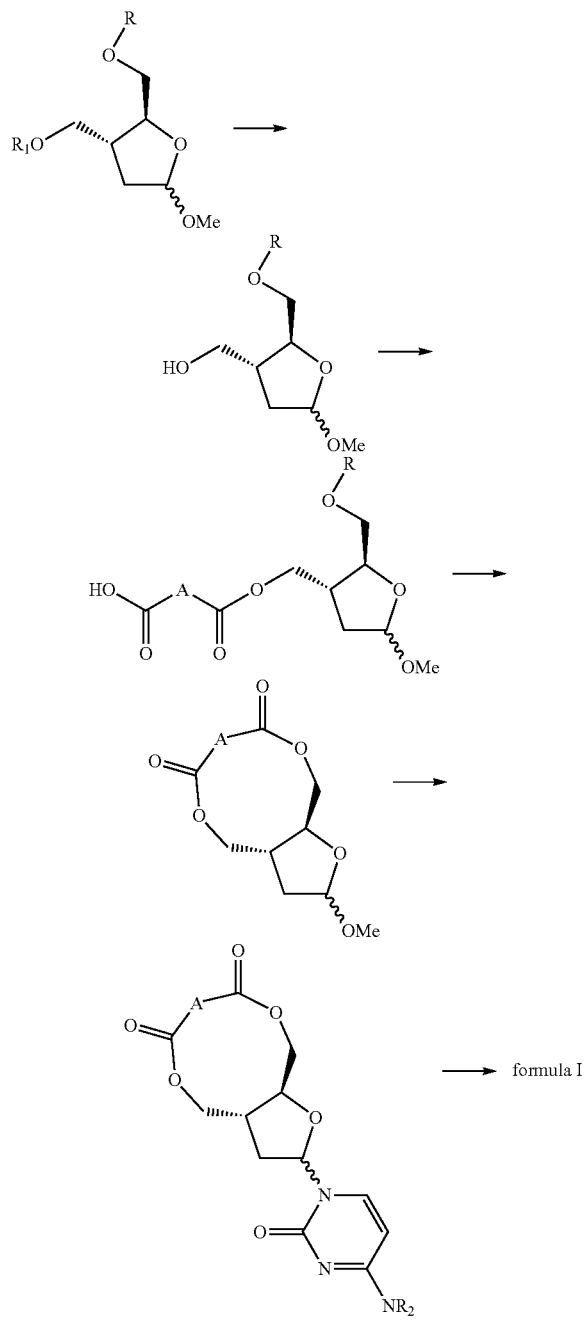

In scheme 3, the above-described differentially protected tetrahydrofuran 4 is first bicyclised and then Vorbrüggen condensed. Bicyclisation proceeds via deprotection of a first of the Rs/Rs¹ pair of complementary protection groups. In this case it is the 4-hydroxymethyl function of the tetrahydrofuran which is first freed up ready for acylation, but this general methodology, with appropriate choice of Rs/Rs1 protecting groups can also proceed via removal and acylation of the 5 hydroxymethyl function as the first step to cyclisation.

The choice of 4- or 5-deprotection first is significant in those cases where A in the ωω-dicarboxylic acid HOOC-A-COOH is asymmetric, ie in compounds of formula I wherein m is 2 or 3 and wherein $R^1/R^2$ in the various methylene mers is not identical. For example where A is —CH(OH)CH$_2$— (that is in formula 1, n is 2, $R^1$ in the first methylene group is OH while $R^2$ is H, both $R^1$ and $R^2$ in the second methylene group are H), then the localization of the $R^1$ hydroxy group adjacent the ester bond to the 4 hydroxymethyl function of the tetrahydrofuran intermediate can be assured by deprotecting Rs first and using the activated acid PG-OC—CH$_2$—CH(OH)—COOH, where PG is a conventional carboxy-protecting group, which is of course selected such that its removal conditions harmonise with the intended removal of $RS^1$. Greene provides extensive reactivity charts to facilitate such selection.

Carboxy protecting groups are extensively reviewed in Greene ibid and typically comprise esters such as methyl or substituted methyl esters, for example methoxymethyl, methylthiomethyl, tetrohydropyranyl, tetrahydrofuranyl, methoxyethoxyethyl, benzyloxymethyl, phenacyl, including p-bromo, alpha methyl or p-methoxyphenacyl, diacylmethyl, or N-phthalimidomethyl. Ethyl esters include unsubstituted ethyl and 2,2,2-trichloroethyl, 2-haloethyl, ω-chloralkyl, 2-(trimethylsilyl)ethyl, 2-methylthiethyl, 2-(p-nitrophenylsulfenyl)ethyl, 2-(p-toluenesulfonyl)ethyl and 1-methyl-1-phenethyl. Other esters include t-butyl, cyclopentyl, cyclohexyl, allyl, cinnamyl and phenyl, inclusing m-methylthiophenyl. Benzyl esters include unsubstituted benzyl, triphenylmethyl, diphenylmethyl including bis(o-nitrophenyl)methyl, 9-anthrylmethyl, 2-(9,10-dioxo)anthrylmethyl, dibenzosuberyl, 2,4,6-trimethylbenzyl, p-bromobenzyl, o-nitrobenzyl, p-nitrobenzyl, p-methoxybenzyl, piperonyl, 4-picolyl and p-(P)-benzyl. Silyl esters include trimethylsilyl, triethylsilyl, t-butyldimethylsilyl, i-propyldimethylsilyl and phenyldimethylsilyl. Activated esters include S-t-butyl, S-phenyl, S-2-pyridyl, N-hydroxypiperidinyl, N-hydroxysuccinimidoyl, N-hydroxyphthalimidoyl, and N-hydroxybenzotriazolyl. Miscellaneous ester carboxy protecting groups include O-acyl oximes, 2,4-dinitrophenylsulfenyl, 2-alkyl-1,3-oxazolines, 4-alkyl-5-oxox-1,3-oxazolidines and 5-alkyl-4-oxo-1,3-dioxolanes. Stannyl esters include diethylstannyl and tri-n-butylstannyl. Non-ester carboxy-protecting groups include amides such as N—N-dimethyl, pyrrolidinyl, piperidinyl, o-nitrophenyl, 7-nitroindolyl, 8-nitrotetrahydroquinolyl and p-(P)benzenesulfonamide. Non-ester carboxy-protecting groups also include hydrazides, such as N-phenylhydrazide or N,N'-diisopropylhydrazide.

An alternative scheme towards differentially protected tetrohydrofuran derivatives is shown in Scheme 4:

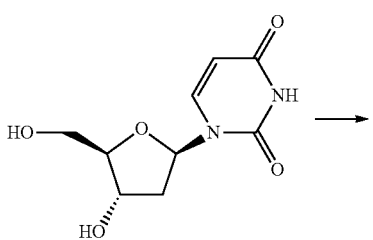

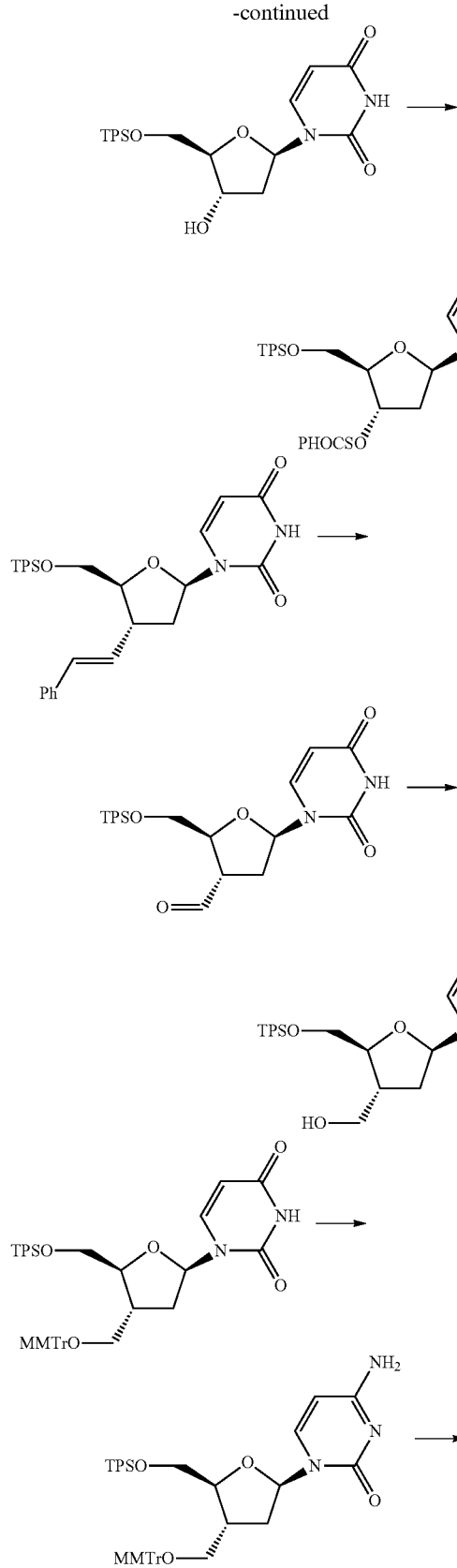

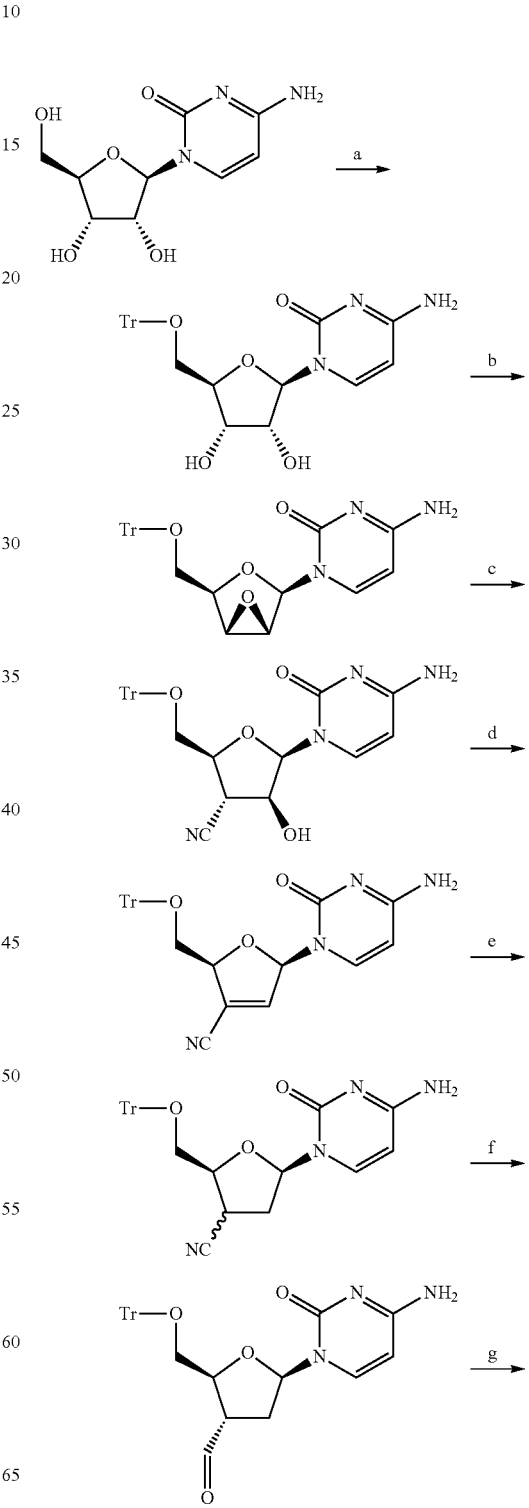

in Sanghvi et al Synthesis 1994, 1163, Sanghvi et al Tett Lett vol 35 p 4697 (1994) and Haly & Sanghvi Nucleosides & Nucleotides Vol 15 1383 (1996). Conversion of the uridine to cytosine analogues is shown in Kozlov, Nucleosides & Nucleotides vol 17 2249 (1998).

An alternative route to differentially protected tetrahydrofurans not requiring conversion of the base i is shown in Scheme 5:

Scheme 4 is extensively reported in the academic literature. The preparation of the uridine analogue precursors is shown

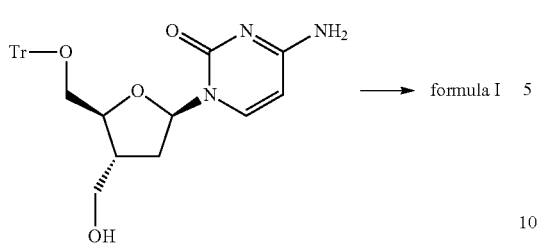

a: TrCl, pyridine, b: i) MsCl, Pyr ii) 1 N NaOH, THF, c) i) EtAlCN, 65C, ii) toluene/THF, d) i) MsCl, Et₃N, ii) EtOAc, f) i) NaBH₄ ii) EtOH, α/β 1:3-4, g) i) DIBAL, ii) silica gel EtOAc, epimerize α/β 93:7, g) i) NaBH₄, ii) EtOH/CH₂Cl₂.

Although scheme 5 has been illustrated with a TrO protecting group and $R^5R^6$=H, it will be apparent that other variants for the amine and hydroxyl protecting groups will be amenable to this route.

Referring now to all schemes, imines where $R^5$ and $R^6$ together define an =$CR^8R^{8'}$ are typically prepared by condensation of the compound of formula 1 wherein $R^5$ and $R^6$ are, or the corresponding intermediate 5 (optionally de-protected) with a compound of the formula $(CH_3O)_2CHNR^8R^{8'}$, typically in DMF at room temperature, analogously to the procedure in Mauldon et al, Bioorg Med Chem 6 (1998) 577-585. The appropriate formamide acetals are generally prepared from intermediate dialkylformamides and dimethyl sulphate at room temperature. Reaction of the intermediate salt with sodium methoxide provides semiacetals, which are then condensed as described above.

Compounds of formula I wherein $R^5$ is an amide are typically prepared by Akiyama acylation (Chem Pharm Bull 1978, 26, 981) of the N-4 unprotected compound of formula I, or the corresponding intermediate 5, with the appropriate ROOR in $H_2O$/1,4-dioxane. Compounds wherein $R^5$ is an amino acid residue are couple with an N-protected amino acid residue using conventional peptide coupling conditions.

DETAILED DESCRIPTION OF THE EMBODIMENTS

Various embodiments of the methods and compounds of the invention will now be described by way of example only, with reference to the following examples and Figures; in which FIG. 1 is a graph of the plasma concentrations over time of in-vivo metabolite following oral administration of a compound of the invention to rat;

FIG. 2 depicts inhibition of typical TAM strains having a primer rescue phenotype by the parent of the compounds of the invention relative to inhibition of conventional NRTIs, as further discussed in Biological Example 2a;

EXAMPLE 1

Figure 1:
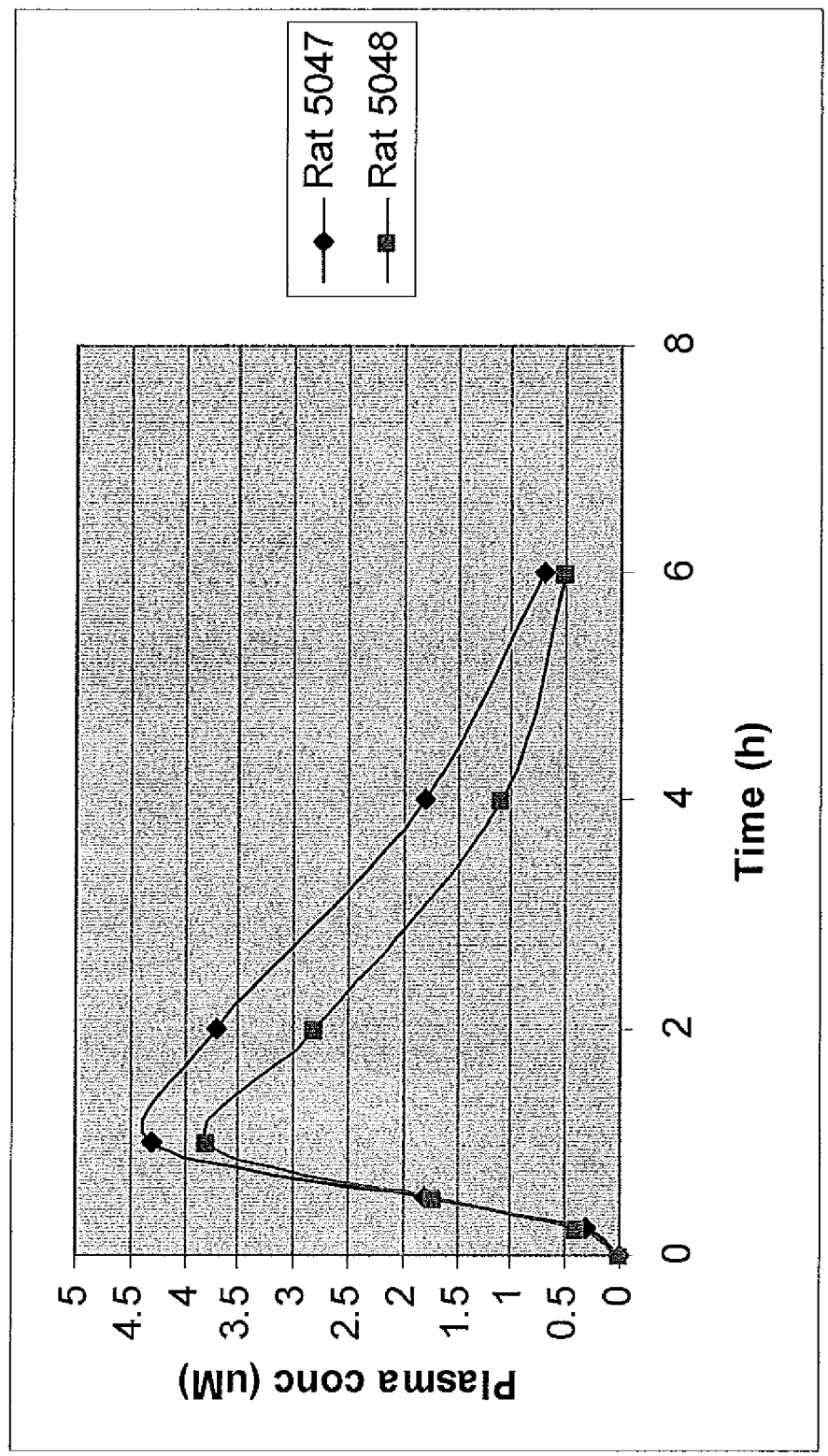

2-(4-amino-2-oxo-2H-pyrimidin-1-yl)-octahydro-1, 5,10-trioxacyclopenta-cyclodecene-6,9-dione

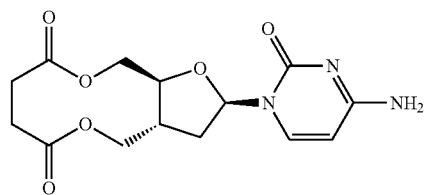

a) (1-{5-(tert-Butyl-diphenyl-silanyloxymethyl)-4-[(4-methoxy-phenyl)-diphenyl-methoxymethyl]-tetrahydro-furan-2-yl}-2-oxo-1,2-dihydro-pyrimidin-4-yl)-carbamic acid tert-butyl ester

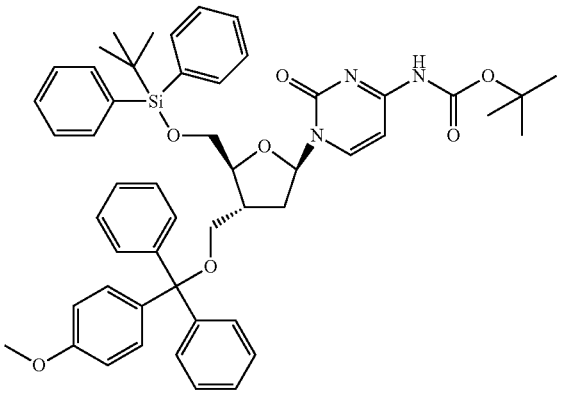

To a solution of 0.75 g (1 mmol) 4-amino-{5-(tert-butyl-silanyloxymethyl)-4-[(4-methoxyphenyl)-diphenyl-methoxymethyl]-tetrahydrofuran-2-yl}-1H-pyrimidin-2-one, prepared as in Scheme 4 above, in dioxan (25 ml) under nitrogen was added a solution of di-tert-butyl dicarbonate (0.44 g, 2 mmol) in dioxan (2 ml). The reaction mixture was stirred at room temperature for 48 hrs. The reaction mixture was evaporated on silica gel and the residue was purified on silica gel column using ethyl acetate/hexanes 2:1 as eluent to give 0.42 g (49%) of the product depicted above.

Proton NMR (CDCl3): 8.33 (d, 1H), 7.64-7.59 (m, 4H), 7.45-7.18 (m, 18H), 6.91 (d, 1H), 6.79-6.77 (m, 2H), 6.10-6.08 (m, 1H), 4.08-4.06 (m, 1H), 3.98-3.96 (m, 1H), 3.77 (s, 3H), 3.59 (dd, 1H), 3.19-3.16 (m, 1H), 3.02-2.98 (m, 1H), 2.57-2.53 (m, 2H), 2.72-2.25 (m, 1H), 1.50 (s, 9H), 1.08 (s, 9H).

b) (1-{5-Hydroxymethyl-4-[(4-methoxy-phenyl)-diphenyl-methoxymethyl]-tetrahydro-furan-2-yl}-2-oxo-1,2-dihydro-pyrimidin-4-yl)-carbamic acid tert-butyl ester

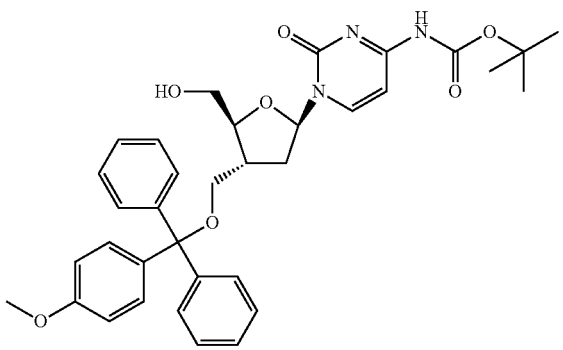

To a solution of the compound above (0.33 g, 0.4 mmol) in tetrahydrofuran (10 ml) was added a solution of TBAF (0.19 g, 0.6 mmol) in tetrahydrofuran (1 ml). The reaction mixture was stirred at room temperature for 3 hrs. The reaction mixture was evaporated on silica gel and the residue was purified on silica gel column using ethyl acetate/hexanes 2:1 as the eluent. Evaporation of appropriate factions gave 0.20 g (80%) of (1-{5-hydroxymethyl-4-[(4-methoxyphenyl-diphenyl-methoxymethyl]-tetrahydrofuran-2-yl}-2-oxo-1,2-dihydro-pyrimidin-4-yl]-carbamic acid tert.-butyl ester.

Proton NMR (CDCl3): 8.22 (d, 1H), 7.40-7.38 (m, 4H), 7.38-7.23 (m, 10H), 6.85-6.82 (m, 1H), 6.03-6.00 (m, 1H), 4.04-3.94 (m, 2H), 3.85-3.81 (m, 1H), 3.80 (s, 3H), 3.29 (dd, 1H), 3.11 (dd, 1H), 2.35-2.22 (m, 3H), 1.52 (s, 9H).

c) Succinic acid mono-{5-(4-tert-butoxycarbony-lamino-2-oxo-2H-pyrimidin-1-yl)-3-[(4-methoxy-phenyl)-diphenyl-methoxymethyl]-tetrahydro-furan-2-yl-methyl}ester

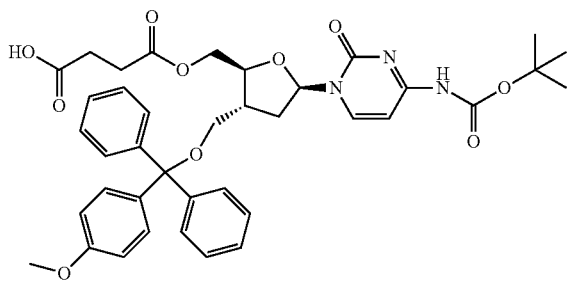

To a solution of the compound above (200 mg, 0.33 mmol) and 4-dimethylaminopyridine (98 mg, 0.8 mmol) in dichloromethane (20 ml) was added succinic anhydride (80 mg, 0.8 mmol). The reaction mixture was stirred at room temperature over night where after the reaction mixture was added to a mixture of dichloromethane and sat. ammonium chloride. The organic phase was washed with water and dried. Evaporation of the solvent gave 222 mg (94%) of the compound depicted above.

Proton NMR (CDCl3): 8.02 (d, 1H), 7.38-7.36 (m, 4H), 7.30-7.15 (m, 9H), 6.84-6.81 (m, 2H), 5.89-5.87 (m, 1H), 4.58 (dd, 1H), 4.26 (dd, 1H), 4.13-4.08 (m, 1H), 3.79 (s, 3H), 3.24 (dd, 1H), 3.05 (t, 1H), 2.80-2.60 (m, 4H). 2.31-2.26 (m, 1H), 2.17-2.12 (m, 2H), 1.51 (s, 9H).

d) Succinic acid mono-[5-(4-tert-butoxycarbony-lamino-2-oxo-2H-pyrimidin-1-yl)-3-hydroxymethyl-tetrahydro-furan-2-yl-methyl]ester

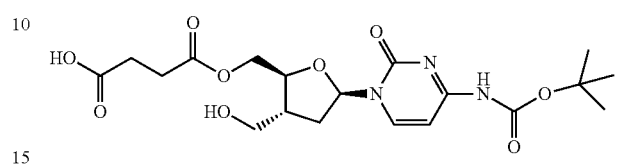

A solution of the compound above (222 mg, 0.31 mmol) in acetic acid (10 ml) and water (5 ml) was stirred at room temperature for 3 hrs. LC/MS indicated complete conversion of the starting material to the desired deprotected compound with a M+1 ion of 442. The reaction mixture was evaporated to dryness and the residue was purified on a C-8 reverse phase column eluted with acetonitrile/water 1:1.5 as eluent to give 100 mg (73%) of the desired compound depicted above.

Proton NMR (CDCl3): 8.18 (d, 1H), 7.23 (d, 1H), 5.93 (broad s, 1H), 4.66-4.63 (m; 1H), 4.33 (d, 1H), 4.15 (broad s, 1H), 3.66 (broad s, 2H), 2.80-2.59 (m, 4H), 2.37 (broad s, 2H), 2.28-2.44 (m, 1H), 1.51 (s, 9H).

e) [1-(6,9-Dioxo-decahydro-1,5,10-trioxa-cyclopen-tacyclodecen-2-yl)-2-oxo-1,2-dihydro-pyrimidin-4-yl]-carbamic acid tert-butyl ester

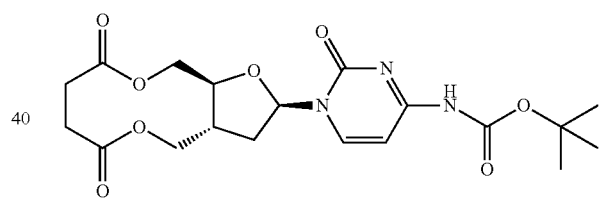

To a solution of the compound above (74 mg, 0.168 mmol), HOBT (27 mg, 0.2 mmol) and triethylamine (0.14 ml, 1 mmol) in dichloromethane (65 ml) and DMF (2 ml) was added EDAC (39 mg, 0.2 mmol). The reaction mixture was stirred at room temperature for 48 hrs where after the reaction mixture was poured into dichloromethane (100 ml) and aq. Citric acid (100 ml). The organic phase was washed with sodium hydrogen carbonate solution and brine. The organic phase was dried over sodium sulfate and evaporated to a residue which purified on a silica gel column using ethyl acetate as the eluent to give 22 mg (31%) of the compound shown above.

Proton NMR (CDCl3): 7.75 (d, 1H), 7.36 (broad s, 1H), 7.25 (d, 1H), 6.02-5.99 (m, 1H), 4.58 (dd, 1H), 4.36-4.28 (m, 2H), 4.14 (t, 2H), 2.64 (s, 4H), 2.58-2.55 (m, 1H), 2.29-2.25 (m, 2H), 1.52 (s, 9H).

f) 2-(4-Amino-2-oxo-2H-pyrimidin-1-yl)-octahydro-1,5,10-trioxa-cyclopenta cyclodecene-6,9-dione To a solution of the compound above (22 mg, 0.052 mmol) in dichloromethane (2 ml) was added trifluoroacetic acid (2 ml). The reaction mixture was stirred at room temperature for 1 h and evaporated to dryness. Co-evaporation twice with toluene gave after careful drying 12.7 mg of the captioned compound as the bis-trifluoracetate salt. LC/MS confirmed the structure with characteristic ions of 324 (M+1) and 647 (2M+1) and the HPLC purity was above 90% at 254 nm.

EXAMPLE 2

7-amino-2-(4-amino-2-oxo-2H-pyrimidin-1-yl)-octahydro-1,5,10-trioxacyclopentacyclodecene-6,9-dione

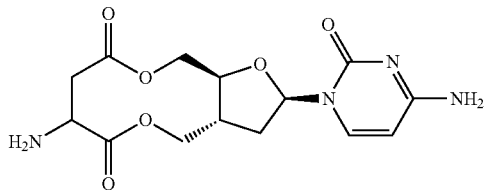

a) 2-tert-Butoxycarbonylamino-succinic acid 4-{5-(4-tert-butoxycarbonylamino-2-oxo-2H-pyrimidin-1-yl]-3-[(4-methoxy-phenyl)-diphenyl-methoxymethyl]-tetrahydro-furan-2-yl-methyl}ester

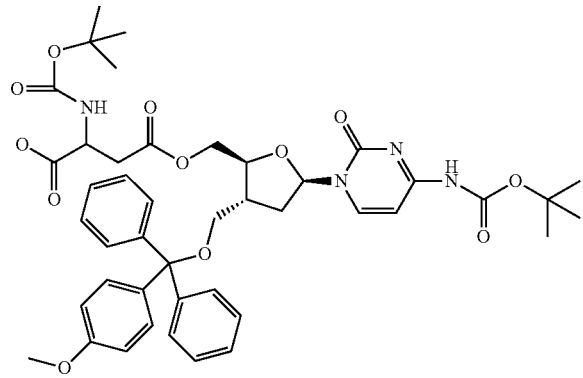

To a solution of (1-{5-hydroxymethyl-4-[(4-methoxyphenyl-diphenyl-methoxymethyl]-tetrahydrofuran-2-yl}-2-oxo-1,2-dihydro-pyrimidin-4-yl]-carbamic acid tert.-butyl ester [98 mg, 0.4 mmol, described in Example 1] and 4-methylaminopyridine (98 mg, 0.8 mmol) in dichloromethane (20 ml) was added N-Boc-(S)-asp anhydride [172 mg, 0.8 mmol (prepared as described in J. Med. Chem. 1971, pp 24-30)]. The reaction mixture was stirred at room temperature over night where after the reaction mixture was poured into ethyl acetate (150 ml) and sat. ammonium chloride (100 ml). The organic phase was washed with water, dried with sodium sulfate and evaporated to give a 371 mg of a crude product depicted above that was used without any purification in the next step.

Proton NMR (CDCl3): 7.76 (d, 1H), 7.38-7.20 (m, 12H), 7.08 (d, 1H), 6.83 (d, 2H), 6.13 (d, 1H), 5.80 (d, 1H), 4.83 (t, 1H), 4.61-4.58 (m, 1H), 4.14-4.06 (m, 2H), 3.79 (s, 3H), 3.25-3.23 (m, 1H), 3.17-3.12 (m, 1H), 3.00 (t, 1H), 2.80-2.76 (m, 1H), 2.26-2.15 (m, 3H), 1.56 (s, 9H), 1.4 (s, 9H).

b) 2-tert-Butoxycarbonylamino-succinic acid 4-[5-(4-tert-butoxycarbonylamino-2-oxo-2H-pyrimidin-1-yl)-3-hydroxymethyl-tetrahydro-furan-2-yl-methyl] ester

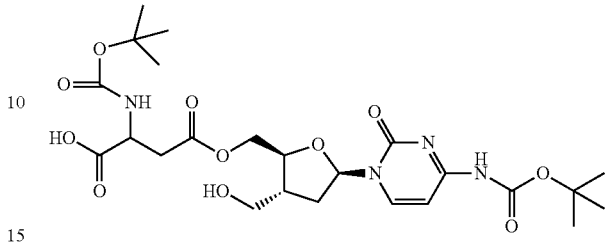

A solution of the compound above (330 mg, 0.40 mmol) in acetic acid (10 ml) and water (5 ml) was stirred at room temperature over night. The reaction mixture was evaporated to dryness and the residue was purified on a C-8 reverse phase column eluted with acetonitrile/water 1:1.5 as eluent to give 72 mg (32%) of the desired compound. LC/MS confirmed the correct structure with a molecular ion of 557 (M+1).

c) [1-(7-tert-butoxycarbonylamino-6,9-dioxo-decahydro-1,5,10-trioxa-cyclopentacyclodecen-2-yl)-2-oxo-1,2-dihydro-pyrimidin-4-yl}-carbamic acid tert-butyl ester

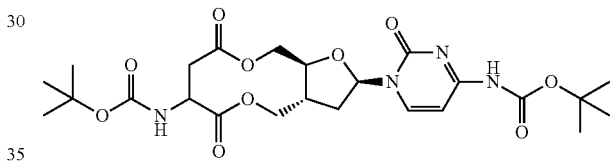

To a solution of the compound above (72 mg, 0.13 mmol), HOBT (20 mg, 0.16 mmol) and triethylamine (0.07 ml, 0.5 mmol) in dichloromethane (50 ml) and DMF (1 ml) was added EDAC (31 mg, 0.16 mmol). The reaction mixture was stirred at room temperature for 24 hrs where after the reaction mixture was poured into dichloromethane (100 ml) and the organic phase was washed with citric acid solution, sodium hydrogen carbonate solution and brine. The organic phase was dried over sodium sulfate and evaporated to a residue which purified on a silica gel column using ethyl acetate as the eluent to give 26 mg (37%) of the compound shown above. LC/MS gave the correct M+1 ion of 539 and M−1 ion of 537.

Proton NMR (CDCl3): 7.73 (d, 1H), 7.40 (broad s, 1H), 7.24 (d, 1H), 6.02-6.00 (m, 1H), 5.26-5.24 (m, 1H), 4.87-4.85 (m, 1H), 4.64-4.55 (m, 2H), 4.20-4.18 (m, 1H), 4.06 (t, 1H), 3.84 (t, 1H), 3.00-2.90 (m, 1H), 2.76-2.66 (m, 1H), 2.57-2.52 (m, 1H), 2.31-2.17 (m, 2H), 1.52 (s, 9H), 1.45 (s, 9H).

d) 7-amino-2-(4-amino-2-oxo-2H-pyrimidin-1-yl)-octahydro-1,5,10-trioxacyclopentacyclodecene-6,9-dione

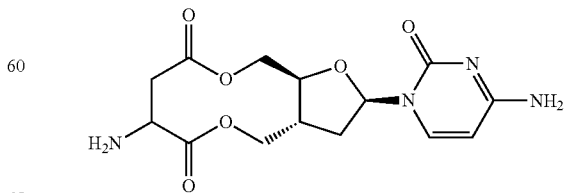

To a solution of the compound above (26 mg, 0.05 mmol) in dichloromethane (2 ml) was added trifluoroacetic acid (2 ml). The reaction mixture was stirred at room temperature for 2 h and evaporated to dryness. Co-evaporation twice with toluene gave after careful drying 24 mg of the title compound as the bis trifluoroacetate salt. LC/MS confirmed the structure with characteristic ions of 339 (M+1), 677 (2M+1) and 337 (M−1).

EXAMPLE 3

2-(4-Amino-2-oxo-2H-pyrimidin-1-yl)-octahydro-1,5,11-trioxacyclopentacycloundecene-6,10-dione

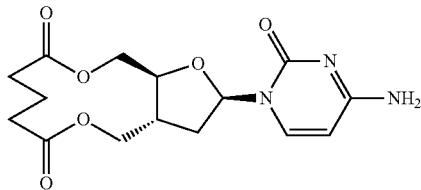

a) Hexanedioic acid mono-{5-[4-tert-butoxycarbonylamino-2-oxo-2H-pyrimidin-1-yl]-3-[(4-methoxyphenyl)-diphenyl-methoxymethyl]-tetrahydro-furan-2-yl-methyl}ester

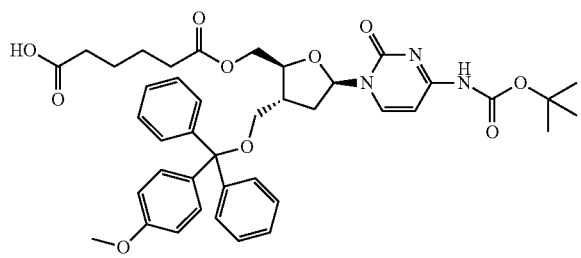

To a solution of (1-{5-hydroxymethyl-4-[(4-methoxyphenyl-diphenyl-methoxymethyl]-tetrahydrofuran-2-yl}-2-oxo-1,2-dihydro-pyrimidin-4-yl]-carbamic acid tert.-butyl ester [730 mg, 1.19 mmol, described in Example 1] and 4-methylaminopyridine (350 mg, 2.86 mmol) in dichloromethane (80 ml) was added glutaric anhydride (327 mg, 2.86 mmol. The reaction mixture was stirred at room temperature over night where after the reaction mixture was poured into dichloromethane. The organic phase was washed with diluted ammonium chloride solution, diluted citric acid solution, water and brine and dried with sodium sulfate and evaporated to give 819 mg (95%) of a crude product depicted above that was used without any purification in the next step.

b) Hexanedioic acid mono-[5-[4-tert-butoxycarbonylamino-2-oxo-2H-pyrimidin-1-yl]-3-hydroxymethyl-tetrahydro-furan-2-yl-methyl]ester

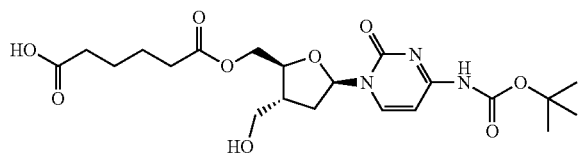

A solution of the compound above (1.09 g, 1.5 mmol) in acetic acid (50 ml) and water (25 ml) was stirred at room temperature for 2.5 hrs. The reaction mixture was evaporated to dryness and the residue was purified on a silica gel column eluted with EtOAc/MeOH 9:1 as eluent to give 435 mg (64%) of the desired compound.

c) [1-(6,10-Dioxo-decahydro-1,5,11-trioxa-cyclopentacycloundecen-2-yl)-2-oxo-1,2-dihydro-pyrimidin-4-yl}-carbamic acid tert-butyl ester

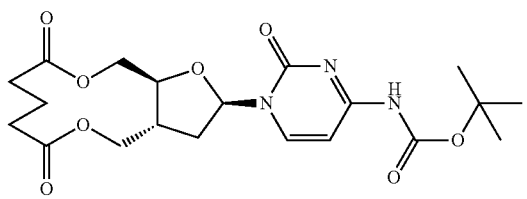

To a solution of the compound above (395 mg, 0.87 mmol), HOBT (235 mg, 1.74 mmol) and DMAP (213 mg, 1.74 mmol) in DMF (120 ml) was added EDAC (334 mg, 1.74 mmol). The reaction mixture was stirred at room temperature for 48 hrs where after the solvent was evaporated. Dichloromethane was added to the reaction residue and it was diluted ammonium chloride solution, diluted citric acid solution water and brine, dried over sodium sulfate and evaporated to give 350 mg of a crude product. LC/MS showed that the desired product with ions at 438 (M+1), 496 (M+acetate), 875 (2M+1) and 436 (M−1). Two purifications on a C-8 reverse phase column eluted with acetonitrile/water 1:1 and acetonitrile/water 1:1.25 gave, after evaporation and lyophilization, 31 mg of the title compound with a purity of about 50% as determined by HPLC at 220 nM.

d) 2-(4-amino-2-oxo-2H-pyrimidin-1-yl)-octahydro-1,5,11-trioxa-cyclopentacycloundecene-6,10-dione

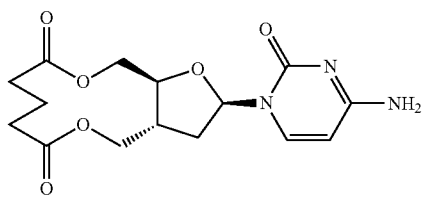

To a solution at ±0° C. of the compound above (31 mg) in dichloromethane (2 ml) was added trifluoroacetic acid (2 ml). The reaction mixture was stirred at ±0° C. for 2 h and then at room temperature for another 2 h. Thereafter the reaction mixture was evaporated to dryness and finally co-evaporation with toluene gave a crude product that was purified on C-8 reverse phase column eluted with acetonitrile/water 1:2. The appropriate fractions were evaporated after addition of TFA and 31 mg of the title compound as the trifluoroacetate salt was obtained. LC/MS confirmed the structure with characteristic ions of 338 (M+1), 396 (M+acetate) and 675 (2M+1) and the purity at 220 nM was about 70%.

BIOLOGY EXAMPLE 1A

Rat Pharmacokinetics

The compound of Example 1 was dissolved in MQ grade water, 3 mg/ml and orally administered to duplicate rats. The dose was 15 mg/kg and plasma samples were taken at t0, 15 & 30 minutes, 1, 2, 4 and 6 hours. Recovery (as the metabolite 2',3'-dideoxy-3'-C-hydroxymethyl-β-D-erythropentofuranosylcytosine) in the plasma was measured with mass spectrometry, detected as the sodium adduct m/z 264 (M+Na)+.

As can be seen in FIG. 1, the compound of the invention provided a substantial plasma concentration of the metabolite 2',3'-dideoxy, 3'-C-hydroxymethyl-β-D-erythropentofuranosylcytosine with a peak concentration at this dose of around 4 uM. As rats cannot be infected with HIV, the antiretroviral activity of this formulation cannot be directly measured in this example, but it is noted that the $ED_{50}$ for the metabolite 2',3'-dideoxy, 3'-C-hydroxymethyl-β-D-erythropento-furanosylcytosine is typically around 0.01 uM in human H9 cells. This in turn means that the peak plasma concentration is several hundredfold over the $ED_{50}$. Other pharmaceutical parameters such as AUC and clearance are consistent with achieving a 24 hour trough level well over the $ED_{50}$ with QD or BID dosing.

BIOLOGICAL EXAMPLE 1B

Permeability

This example measures transport of inhibitors through the cells of the human gastroenteric canal. The assay uses the well known Caco-2 cells with a passage number between 40 and 60.

Apical to Basolateral Transport

Generally every compound will be tested in 2-4 wells. The basolateral and the apical wells will contain 1.5 mL and 0.4 mL transport buffer (TB), respectively, and the standard concentration of the tested substances is 10 μM. Furthermore all test solutions and buffers will contain 1% DMSO. Prior to the experiment the transport plates are pre-coated with culture medium containing 10% serum for 30 minutes to avoid nonspecific binding to plastic material. After 21 to 28 days in culture on filter supports the cells are ready for permeability experiments.

Transport plate no 1 comprises 3 rows of 4 wells each. Row 1 is denoted Wash, row 2 "30 minutes" and row 3 "60 minutes". Transport plate no 2 comprises 3 rows of 4 wells, one denoted row 4 "90 minutes", row 5 "120 minutes and the remaining row unassigned.

The culture medium from the apical wells is removed and the inserts are transferred to a wash row (No. 1) in a transport plate (plate no. 1) out of 2 plates without inserts, which have already been prepared with 1.5 mL transport buffer (HBSS, 25 mM HEPES, pH 7.4) in rows 1 to 5. In A→B screening the TB in basolateral well also contains 1% Bovine Serum Albumin.

0.5 mL transport buffer (HBSS, 25 mM MES, pH 6.5) is added to the inserts and the cell monolayers equilibrated in the transport buffer system for 30 minutes at 37° C. in a polymix shaker. After being equilibrated to the buffer system the Transepithelial electrical resistance value (TEER) is measured in each well by an EVOM chop stick instrument. The TEER values are usually between 400 to 1000Ω per well (depends on passage number used).

The transport buffer (TB, pH 6.5) is removed from the apical side and the insert is transferred to the 30 minutes row (No. 2) and fresh 425 μL TB (pH 6.5), including the test substance is added to the apical (donor) well. The plates are incubated in a polymix shaker at 37° C. with a low shaking velocity of approximately 150 to 300 rpm.

After 30 minutes incubation in row 2 the inserts will be moved to new pre-warmed basolateral (receiver) wells every 30 minutes; row 3 (60 minutes), 4 (90 minutes) and 5 (120 minutes).

25 μL samples will be taken from the apical solution after ~2 minutes and at the end of the experiment. These samples represent donor samples from the start and the end of the experiment.

300 μL will be taken from the basolateral (receiver) wells at each scheduled time point and the post value of TEER is measured at the end the experiment. To all collected samples acetonitrile will be added to a final concentration of 50% in the samples. The collected samples will be stored at −20° C. until analysis by HPLC or LC-MS.

Basolateral to Apical Transport

Generally every compound will be tested in 2-4 wells. The basolateral and the apical wells will contain 1.55 mL and 0.4 mL TB, respectively, and the standard concentration of the tested substances is 10 μM. Furthermore all test solutions and buffers will contain 1% DMSO. Prior to the experiment the transport plates are precoated with culture medium containing 10% serum for 30 minutes to avoid nonspecific binding to plastic material.

After 21 to 28 days in culture on filter supports the cells are ready for permeability experiments. The culture medium from the apical wells are removed and the inserts are transferred to a wash row (No. 1) in a new plate without inserts (Transport plate).

The transport plate comprises 3 rows of 4 wells. Row 1 is denoted "wash" and row 3 is the "experimental row". The transport plate has previously been prepared with 1.5 mL TB (pH 7.4) in wash row No. 1 and with 1.55 mL TB (pH 7.4), including the test substance, in experimental row No. 3 (donor side).

0.5 mL transport buffer (HBSS, 25 mM MES, pH 6.5) is added to the inserts in row No. 1 and the cell monolayers are equilibrated in the transport buffer system for 30 minutes, 37° C. in a polymix shaker. After being equilibrated to the buffer system the TEER value is measured in each well by an EVOM chop stick instrument.

The transport buffer (TB, pH 6.5) is removed from the apical side and the insert is transferred to row 3 and 400 μL fresh TB, pH 6.5 is added to the inserts. After 30 minutes 250 μL is withdrawn from the apical (receiver) well and replaced by fresh transport buffer. Thereafter 250 μL samples will be withdrawn and replaced by fresh transport buffer every 30 minutes until the end of the experiment at 120 minutes, and finally a post value of TEER is measured at the end of the experiment. A 25 μL samples will be taken from the basolateral (donor) compartment after ~2 minutes and at the end of the experiment. These samples represent donor samples from the start and the end of the experiment.

To all collected samples acetonitrile will be added to a final concentration of 50% in the samples. The collected samples will be stored at −20° C. until analysis by HPLC or LC-MS.

Calculation

Determination of the cumulative fraction absorbed, $FA_{cum}$, versus time. $FA_{cum}$ is calculated from:

$$FA_{cum} = \sum \frac{C_{Ri}}{C_{Di}}$$

Where $C_{Ri}$ is the receiver concentration at the end of the interval i and $C_{Di}$ is the donor concentration at the beginning of interval i. A linear relationship should be obtained.

The determination of permeability coefficients ($P_{app}$, cm/s) are calculated from:

$$P_{app} = \frac{(k \cdot V_R)}{(A \cdot 60)}$$

where k is the transport rate (min$^{-1}$) defined as the slope obtained by linear regression of cumulative fraction absorbed ($FA_{cum}$) as a function of time (min), $V_R$ is the volume in the receiver chamber (mL), and A is the area of the filter (cm$^2$).

Reference Compounds

| Category of absorption in man | Markers | % absorption in man |
|---|---|---|
| PASSIVE TRANSPORT | | |
| Low (0-20%) | Mannitol | 16 |
| | Methotrexate | 20 |
| Moderate (21-75%) | Acyclovir | 30 |
| High (76-100%) | Propranolol | 90 |
| | Caffeine | 100 |
| ACTIVE TRANSPORT | | |
| Amino acid transporter | L-Phenylalanine | 100 |
| ACTIVE EFFLUX | | |
| PGP-MDR1 | Digoxin | 30 |

BIOLOGY EXAMPLE 2

Activity against TAM primer rescue-related resistant HIV in the PhenoSense HIV assay The susceptibility of the compounds of the invention, measured as the plasma metabolite 2',3'-dideoxy, 3'-C-hydroxymethyl-β-D-erythropentofuranosylcytosine on HIV-1 isolates from patient plasma samples that bear typical TAM primer rescue mutant resistant genotypes is determined by the commercially available PhenoSense HIV assay (described in Petropoulos, C J et al., (2000) Antimicrob. Agents Chemother. 44:920-928 and performed by ViroLogics, Inc). The assay is performed by amplifying the protease (PR)-RT segment of the HIV pol gene from patient plasma and inserting the amplification products into a modified HIV-1 vector derived from an NL4-3 molecular clone.

Viral stocks are prepared by co-transfecting 293 cell cultures with recombinant viral DNA vector and an expression vector that produces the amphotropic murine leukemia virus envelope proteins. Pseudotyped virus particles are harvested from the transfected cell cultures and are used to infect fresh 293 cell cultures. The recombinant viral DNA contains a luciferase gene cassette within the HIV env gene region and the production of luciferase in target cells is dependent on the completion of one round of virus replication. Drug susceptibility is measured by adding serial concentrations of the compound of the invention and the reference compounds to the cells. Drugs that inhibit virus replication reduce luciferase signal in a dose-dependent manner, providing a quantitative measure of drug susceptibility.

EXAMPLE 2a

Table 1 summarizes a main cluster of primer-rescue-related TAM mutants used in the experiment are resistant to HIV and bear the characteristic TAM genotype that typically emerges during AZT-involved antiretroviral therapy.

TABLE 1

Characteristic genotype in primer rescue-related TAM patient isolates 20 and 21

| Isolate number | Characteristic primer rescue-related TAM mutations |
|---|---|
| 20 | M41L, D67N, K70R, V118I, L210W, R211K, T215F, K219Q and L228H |
| 21 | M41L, D67N, K70S, V118I, L210W, R211K, T215Y, K219N and L228H |

Figure 2:
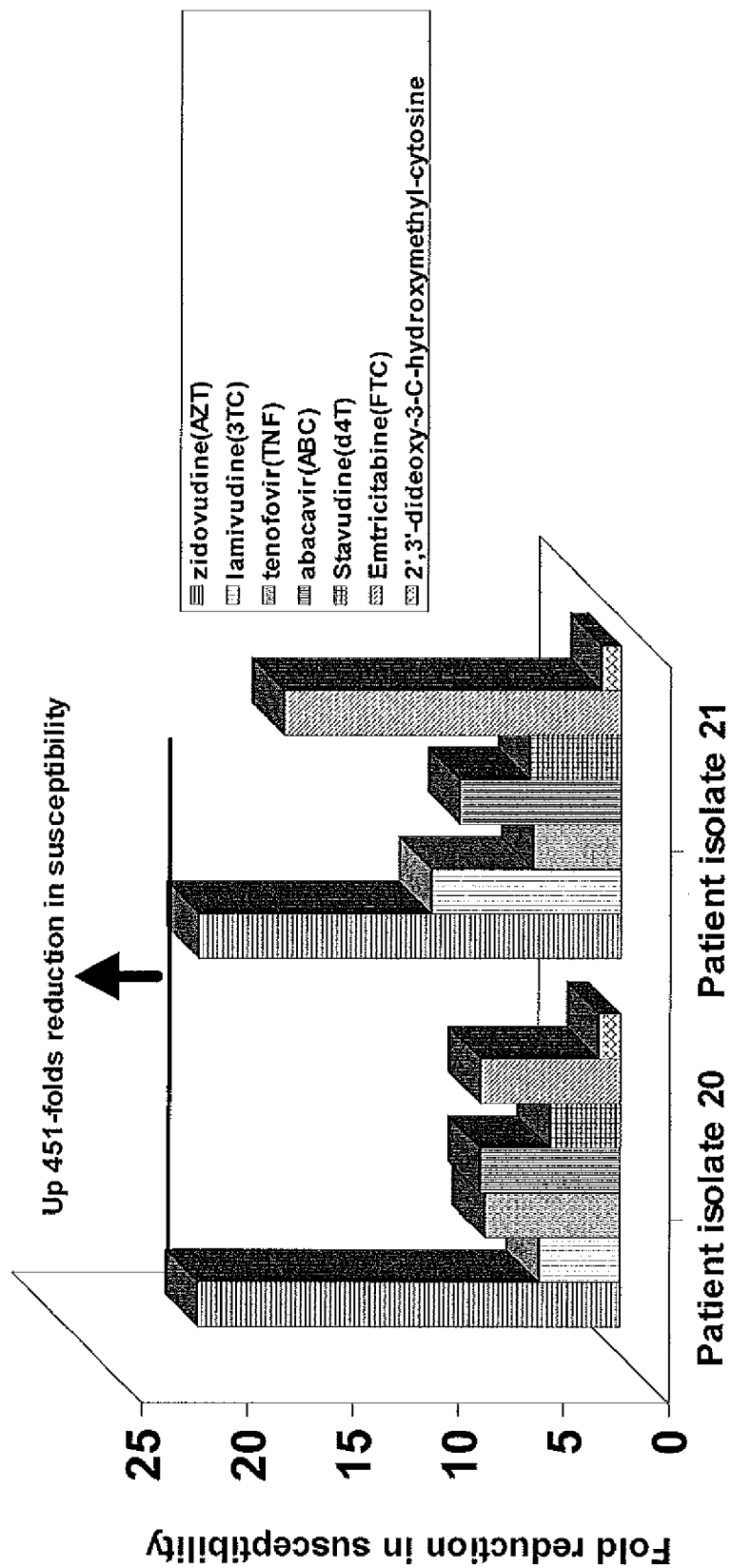

Results are depicted in FIG. 2. Wild-type HIV virus is used as the reference. Here, the inhibition of the patient isolate 20 and 21 strains is expressed as the fold change in reduction of susceptibility to the treatment drug as compared to parallel runs of the reference. The following antiviral drugs were tested: AZT, 3TC, TNF, ABC, d4T, FTC and the compound of the invention, as the plasma metabolite 2',3'-dideoxy, 3'-C-hydroxymethyl-β-D-erythropentofuranosylcytosine. It is clearly apparent that the compound of the invention retained activity against the TAM bearing strains. The results show only a 1.0 fold reduction in susceptibility for the isolate 20 strain and less than a 1.0 fold reduction in susceptibility for the isolate 21 strain. This means that the compounds of the invention retained activity against the patient's primer rescue-related mutant HIV RT at a level of potency similar to its potency against wild type HIV RT. In contrast, other drugs, notably AZT (451 fold reduction in susceptibility), but also to 3TC, TFN, ABC, d4T and FTC, lost potency against the virus from these patients as compared to wildtype. In other words, the virus from these patients exhibited resistance, that is large reductions in susceptibility, to these drugs as shown in FIG. 2.

It is important to note that the two patient isolates harbor different amino acid transitions at codon 215; T to F in isolate 20 and T to Y in isolate 21. This is a representative hallmark of primer rescue-related TAM resistance mutants.

EXAMPLE 2b

Table 2 outlines a primer rescue-related mutant HIV with the genetic background M184V (a discriminative mutant), which is typically selected by the very commonly employed antiretroviral therapy AZT+3TC (Combivir).

TABLE 2

Genotypic changes in TAM-primer rescue-related patient isolate 19

| Isolate number | Characteristic primer rescue-related TAM mutations |
|---|---|
| 19 | M41L, D67N, K70R, V118I, M184V, L210W, T215F, K219E and L228H |

Figure 3:
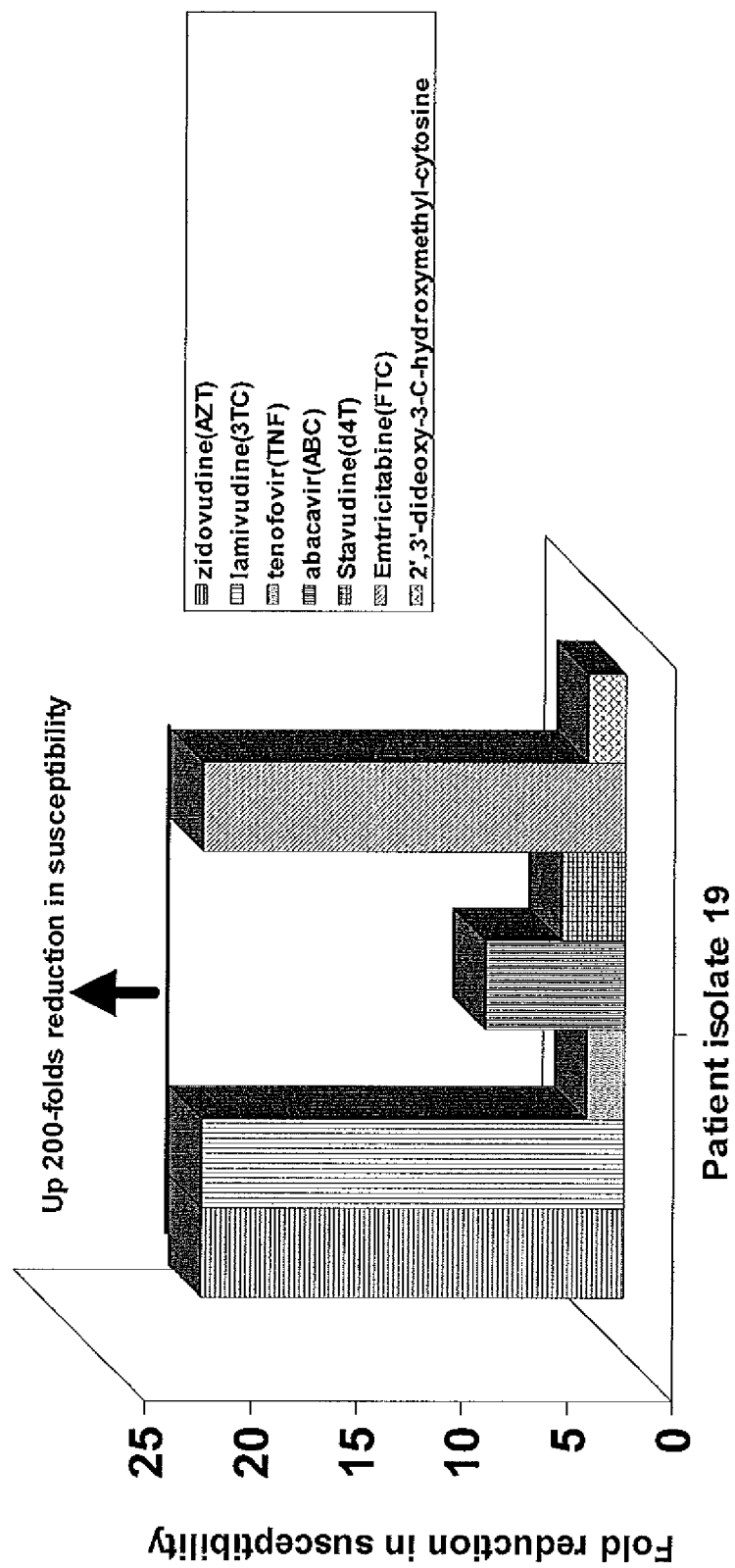
FIG. 3 depicts inhibition of M184V+TAMs having a primer rescue phenotype by the parent of the compounds of the invention, relative to inhibition of conventional NRTIs, as further discussed in Biological Example 2b.

As shown in FIG. 3, the compounds of the invention, as measured by the plasma metabolite 2',3'-dideoxy, 3'-C-hydroxymethyl-β-D-erythropentofuranosylcytosine once again retained activity against this resistant virus, showing only a 1.78-fold difference in susceptibility compared to wild type HIV. Both 3TC and AZT lost activity and showed reduced potency (i.e. a pronounced reduction in viral susceptibility) to the resistance virus (FIG. 3).

EXAMPLE 2c

Continuous challenge of patients with antiretroviral agents results in the emergence of MDR. A T69S mutation with a 6-bp insertion between amino acids 68 and 70 in the finger region of RT is often seen in combination with various forms of TAMs and contributes to an enhanced primer rescue activity. A cluster of MDR (with different forms of amino acid insertion(s)) in combination with TAM was chosen, as outlined in Table 3.

TABLE 3

Genotypic changes in primer rescue-related patient isolates 31, 32 and 35

| Isolate number | Characteristic primer rescue-related TAM mutations |
|---|---|
| 31 | T69S + double amino acid insertion SG in the genetic background of TAMs A62V, D67E and R211K |
| 32 | T69S + double amino acid insertion VG in the genetic background of TAMs A62V, D67G, V75I and T215I |
| 35 | T69S + double amino acid insertion VA in the genetic background of TAMs A62V, R211K, T215Y and L228H |

Figure 4:
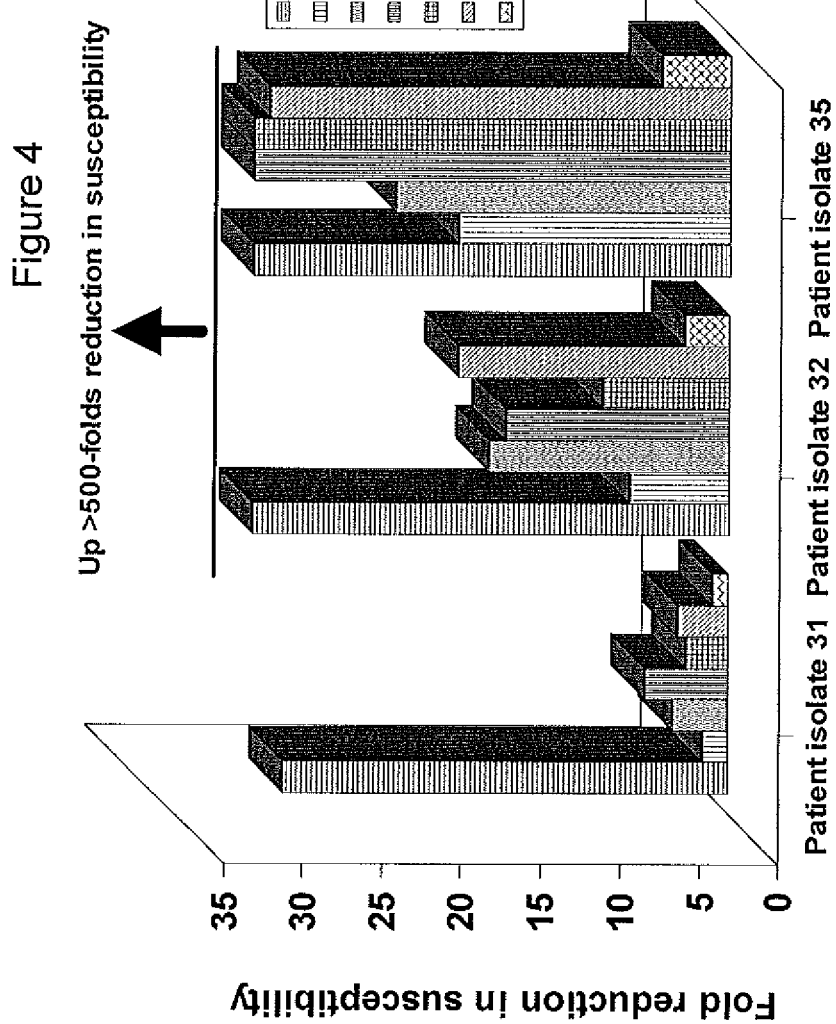
FIG. 4 depicts inhibition of T69S+XX+TAMs by the parent of the compounds of the invention, relative to inhibition of conventional NRTIs, as further discussed in Biological Example 2c.

As shown in FIG. 4, the compound of the invention inhibited these patient isolates, giving the smallest change in drug susceptibility compared with six reference antivirals currently used in conventional antiretroviral therapy.

Note that a pronounced (500 to 1000-fold) reduction in susceptibility to AZT was observed for patient isolates 32 and 35 whereas the compound of the invention showed changes of 2.79 and 4.29-fold respectively. This is consistent with the compound of the invention displaying a different mechanism of inhibition compared to the obligatory DNA chain terminators represented by conventional NRTIs.

EXAMPLE 2d

Isolate 4 represents a further discriminative mutant bearing the K65R+M184V genotype in a non-essential TAM background consisting of mutations at R211S and K219E. This isolate causes a typical cross-resistance to abacavir, 3TC and the newly approved nucleoside FTC, but retains its susceptibility to thymidine analogues, such as AZT and d4T. This isolate does not bear typical primer rescue mutations, yet the compound of the invention still inhibits this viral phenotype as indicated by an FC value of 3.88. This value is comparable to the thymidine analogues, AZT (FC=1.11) and d4T (FC=0.71), whereas significant resistance was found for 3TC (FC>200), FTC (FC>40) and to some extent to ABC (FC>9.0). This experimental data demonstrates that the compound of the invention not only bears unique properties against "primer rescue" mutants but is also able to inhibit HIV mutants from the discriminative family. This, therefore, contrasts with the inhibitory mechanism employed by 3TC and FTC as well as the likely mechanism of 4'-C-ethynyl compounds in which M184V together with one additional amino acid change in codon T165R in the catalytic region contributes to cross-resistance to 4-C-ethynyl nucleoside (Kodama 2002).

BIOLOGICAL EXAMPLE 3

Activity of 2',3'-dideoxy-3-C-hydroxymethyl-cytosine against primer rescue-related resistant HIV in PBMC.

The antiviral performance of the compound of the invention against additional TAM primer rescue-related resistant HIV isolates was assayed in a PBMC culture. Isolates of HIV-1 were generated and expanded to high titer by co-cultivation of infected patient PBMC with PHA-stimulated donor PBMC (Virology Manual for ACTG HIV Laboratories). The cell-free supernatants were harvested, sequenced, and stored in aliquots at −70° C. for drug susceptibility assays.

In vitro drug susceptibility assays were performed using a modified ACTG/DOD consensus method (Virology Manual for ACTG HIV laboratories). PBMCs were pre-infected with viral stocks for 4 hrs at 3TC in a humidified atmosphere of 5% $CO_2$ following 4 hr incubation. Infected cells were washed twice in media and pipetted into a microtiter plate with eight serial drug dilutions. Each well contained 100,000 pre-infected PBMC and all drug dilutions were made with cell culture medium. The drug dilutions were chosen to span the 50% inhibitory concentration ($IC_{50}$) for each single drug. Control wells containing cells and virus were co-incubated on each plate. After a 7-day incubation at 3TC in a mummified atmosphere of 5% $CO_2$, viral growth was determined using a p24 antigen assay on supernatants (Abbott Laboratories, Chicago, USA). The percent inhibition of viral growth compared to the control well, which contained no drug, was calculated and expressed as fold changes (reductions in compounds susceptibility) compared to the control well. The reference compound AZT was run in parallel with the compound of the invention.

A cluster of representative of primer rescue-related mutant virus was selected that harbors the essential feature of primer rescue-related TAM resistant RT mutations. Strains with mutations at position M41L, D67N, K70R, L210W, T215Y/F and K219Q/E in various combinations with or without discriminative mutant M184V were used as indicated in Table 4.

TABLE 4

TAM primer rescue-related genotype in 9 patient isolates

| Isolate number | Characteristic primer rescue-related TAM mutations |
|---|---|
| 1295 | M41L, D67N, K70R, V75M, V118I, M184V, L210W, R211K, T215Y and K219E |
| 7086 | D67N, T69N, K70R, V118I, L210W, T215V and K219Q |
| J12840 | M41L, D67N, V118I, M184V, L210W, R211N, T215Y |
| J10308 | M41L, D67N, M184V, L210W, R211S, T215Y |
| 7141 | M41L, D67N, M184V, H208Y, R211K, T215Y, K219N |
| J14007 | D67N, T69N, K70R, M184V, H208Y, R211K, T215F, K219Q, L228H |
| VA206 | D67N, M184V, L210W, R211K, T215Y |
| VA286 | M41L, E44D, D67N, L74V, V118I, M184I, E203K, H208Y, L210W, R211K, T215Y |

Figure 5:
FIG. 5 depicts inhibition of TAM strains by the parent of the compounds of the invention, relative to inhibition by zidovudine and lamivudine, as further discussed in Biological Example 3

Most of these selected primer rescue mutants conferred a pronounced resistance to AZT susceptibility, dropping a couple of hundred folds in FC value. The exception was isolate 7086 (FC=3.0), which bears the T215V amino acid mutation. A complete report of FC values is presented in FIG. 5. Here, 2',3'-dideoxy-3'-C-hydroxymethylcytosine inhibited all 8-isolates, with the highest FC value being only 2.7.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:
1. A compound of the formula:

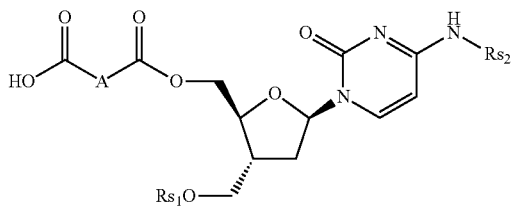

wherein:
A is $(CR^1R^2)_n$;
$R^1$ is independently H, —$OR^3$, —$NHR^4$, $C_1$-$C_4$alkyl; or when n is 2, adjacent $R^1$ can together define an olefinic bond;
$R^2$ is H;
  or when $R^1$ and $R^2$ form gem substitution on the same carbon and $R^1$ is $C_1$-$C_4$alkyl, then $R^2$ is $C_1$-$C_4$alkyl;
  or when $R^1$ and $R^2$ form gem substitution on the same carbon and $R^1$ is $OR^3$, then $R^2$ is —C(=O)OH, or a pharmaceutically acceptable ester thereof;
$R^3$ is independently H, or a pharmaceutically acceptable ester thereof;
$R^4$ is independently H, or a pharmaceutically acceptable amide thereof;
$Rs_1$ is H or a hydroxy protecting group selected from methyl, ethyl, isopropyl, benzyl, triphenylmethyl, tetrahydropyranyl, 4-methoxyphenyl-diphenylmethyl, 2,2,2-trichloroethyl, trimethylsilyl, t.butylsilyl, t.butyldiphenylsilyl, acetyl, propionyl and benzoyl;
$Rs_2$ is H or an amino protecting group selected from benzyloxycarbonyl, substituted benzyloxycarbonyl, 9-fluorenylmethyloxycarbonyl, tert.butyloxycarbonyl, ethoxycarbonyl, diisopropylmethoxycarbonyl, allyloxycarbonyl, cyclopentyloxycarbonyl, adamantyloxycarbonyl, triphenylmethyl, benzyl, trimethylsilyl, phenylthiocarbonyl and dithiasuccinoyl;
n is 1, 2 or 3;
and pharmaceutically acceptable salts thereof.

2. A compound according to claim 1, wherein n is 2.
3. A compound according to claim 2, wherein $R^1$ and $R^2$ are both H.
4. A compound according to claim 3, wherein $Rs_2$ is tert. butyloxycarbonyl.
5. A compound according to claim 1, denoted 4-(((2S,3R,5R)-5-(4-(tert-butoxycarbonylamino)-2-oxopyrimidin-1(2H)-yl)-3-(((4-methoxyphenyl)diphenylmethoxy)methyl)tetrahydrofuran-2-yl)methoxy)-4-oxobutanoic acid, having the structure:

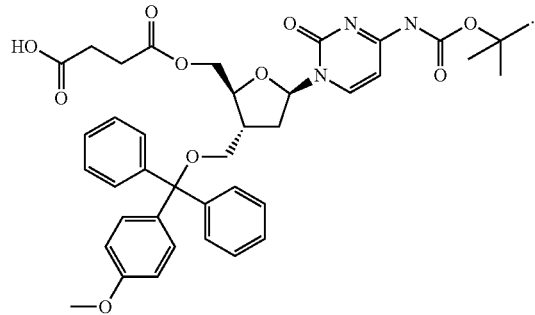

6. A compound according to claim 1, denoted 4-(((2S,3R,5R)-5-(4-(tert-butoxycarbonylamino)-2-oxopyrimidin-1(2H)-yl)-3-(hydroxymethyl)tetrahydrofuran-2-yl)methoxy)-4-oxobutanoic acid, having the structure:

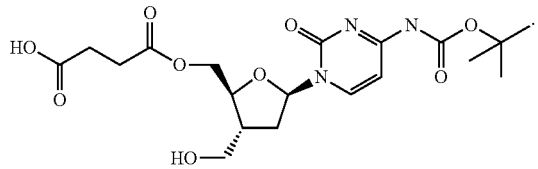

* * * * *